US008633015B2

(12) United States Patent
Ness et al.

(10) Patent No.: US 8,633,015 B2
(45) Date of Patent: Jan. 21, 2014

(54) FLOW-BASED THERMOCYCLING SYSTEM WITH THERMOELECTRIC COOLER

(75) Inventors: Kevin D. Ness, San Mateo, CA (US); Donald A. Masquelier, Tracy, CA (US); Billy W. Colston, Jr., San Ramon, CA (US); Benjamin J. Hindson, Livermore, CA (US)

(73) Assignee: Bio-Rad Laboratories, Inc., Hercules, CA (US)

( * ) Notice: Subject to any disclaimer, the term of this patent is extended or adjusted under 35 U.S.C. 154(b) by 401 days.

(21) Appl. No.: 12/890,550

(22) Filed: Sep. 24, 2010

(65) Prior Publication Data

US 2011/0212516 A1 Sep. 1, 2011

Related U.S. Application Data

(63) Continuation-in-part of application No. 12/586,626, filed on Sep. 23, 2009.

(60) Provisional application No. 61/194,043, filed on Sep. 23, 2008, provisional application No. 61/206,975, filed on Feb. 5, 2009, provisional application No. 61/271,538, filed on Jul. 21, 2009, provisional application No. 61/275,731, filed on Sep. 1, 2009, provisional application No. 61/277,200, filed on Sep. 21, 2009, provisional application No. 61/277,203, filed on Sep. 21, 2009, provisional application No. 61/277,204, filed on Sep. 21, 2009, provisional application No. 61/277,216, filed on Sep. 21, 2009, provisional application No. 61/277,249, filed on Sep. 21, 2009, provisional application No. 61/277,270, filed on Sep. 22, 2009.

(51) Int. Cl.
*C12M 1/34* (2006.01)

(52) U.S. Cl.
USPC .................... 435/287.2; 435/6.12; 435/303.1

(58) Field of Classification Search
USPC ..................................................... 435/303.1
See application file for complete search history.

(56) References Cited

U.S. PATENT DOCUMENTS

| | | |
|---|---|---|
| 3,575,220 A | 4/1971 | Davis et al. |
| 4,051,025 A | 9/1977 | Ito |

(Continued)

FOREIGN PATENT DOCUMENTS

| | | |
|---|---|---|
| EP | 1 522 582 A2 | 4/2005 |
| EP | 1 522 582 B1 | 4/2007 |

(Continued)

OTHER PUBLICATIONS

Young, Lee W., Authorized officer, International Searching Authority, International Search Report, PCT Application Serial No. PCT/US2009/05317; mailing date: Nov. 20, 2009.

(Continued)

*Primary Examiner* — Michael Hobbs
(74) *Attorney, Agent, or Firm* — Kolisch Hartwell, P.C.

(57) ABSTRACT

Thermocycling system, including methods and apparatus, for performing a flow-based reaction on a sample in fluid. The system may include a plurality of segments defining at least two temperature regions, and also may include a plurality of heating elements configured to maintain each temperature region at a different desired temperature. At least one of the heating elements may be a thermoelectric cooler operatively disposed to transfer heat to and/or from a temperature region The system further may include a fluid channel extending along a helical path that passes through the temperature regions multiple times such that fluid flowing in the channel is heated and cooled cyclically.

21 Claims, 14 Drawing Sheets

(56) References Cited

U.S. PATENT DOCUMENTS

| | | | |
|---|---|---|---|
| 4,201,691 | A | 5/1980 | Asher et al. |
| 4,283,262 | A | 8/1981 | Cormier et al. |
| 4,348,111 | A | 9/1982 | Goulas et al. |
| 4,636,075 | A | 1/1987 | Knollenberg |
| 4,948,961 | A | 8/1990 | Hillman et al. |
| 5,055,390 | A | 10/1991 | Weaver et al. |
| 5,176,203 | A | 1/1993 | Larzul |
| 5,225,332 | A | 7/1993 | Weaver et al. |
| 5,270,183 | A | 12/1993 | Corbett et al. |
| 5,314,809 | A | 5/1994 | Erlich et al. |
| 5,344,930 | A | 9/1994 | Riess et al. |
| 5,422,277 | A | 6/1995 | Connelly et al. |
| 5,538,667 | A | 7/1996 | Hill et al. |
| 5,555,191 | A | 9/1996 | Hripcsak |
| 5,585,069 | A | 12/1996 | Zanzucchi et al. |
| 5,587,128 | A | 12/1996 | Wilding et al. |
| 5,602,756 | A | 2/1997 | Atwood et al. |
| 5,720,923 | A | 2/1998 | Haff et al. |
| 5,736,314 | A | 4/1998 | Hayes et al. |
| 5,779,977 | A | 7/1998 | Haff et al. |
| 5,827,480 | A | 10/1998 | Haff et al. |
| 5,856,174 | A | 1/1999 | Lipshutz et al. |
| 5,912,945 | A | 6/1999 | Da Silva et al. |
| 5,928,907 | A | 7/1999 | Woudenberg et al. |
| 5,945,334 | A | 8/1999 | Besemer et al. |
| 5,972,716 | A | 10/1999 | Ragusa et al. |
| 5,980,936 | A | 11/1999 | Krafft et al. |
| 5,994,056 | A | 11/1999 | Higuchi |
| 6,033,880 | A | 3/2000 | Haff et al. |
| 6,042,709 | A | 3/2000 | Parce et al. |
| 6,057,149 | A | 5/2000 | Burns et al. |
| 6,126,899 | A | 10/2000 | Woudenberg et al. |
| 6,130,098 | A | 10/2000 | Handique et al. |
| 6,143,496 | A | 11/2000 | Brown et al. |
| 6,146,103 | A | 11/2000 | Lee et al. |
| 6,171,785 | B1 | 1/2001 | Higuchi |
| 6,175,669 | B1 | 1/2001 | Colston et al. |
| 6,176,609 | B1 | 1/2001 | Cleveland et al. |
| 6,177,479 | B1 | 1/2001 | Nakajima et al. |
| 6,210,879 | B1 | 4/2001 | Meloni et al. |
| 6,258,569 | B1 | 7/2001 | Livak et al. |
| 6,281,254 | B1 | 8/2001 | Nakajima et al. |
| 6,303,343 | B1 | 10/2001 | Kopf-Sill |
| 6,357,907 | B1 | 3/2002 | Cleveland et al. |
| 6,384,915 | B1 | 5/2002 | Everett et al. |
| 6,391,559 | B1 | 5/2002 | Brown et al. |
| 6,440,706 | B1 | 8/2002 | Vogelstein et al. |
| 6,466,713 | B2 | 10/2002 | Everett et al. |
| 6,488,895 | B1 | 12/2002 | Kennedy |
| 6,489,103 | B1 | 12/2002 | Griffiths et al. |
| 6,494,104 | B2 | 12/2002 | Kawakita et al. |
| 6,509,085 | B1 | 1/2003 | Kennedy |
| 6,521,427 | B1 | 2/2003 | Evans |
| 6,524,456 | B1 | 2/2003 | Ramsey et al. |
| 6,540,895 | B1 | 4/2003 | Spence et al. |
| 6,551,841 | B1 | 4/2003 | Wilding et al. |
| 6,558,916 | B2 | 5/2003 | Veerapandian et al. |
| 6,575,188 | B2 | 6/2003 | Parunak |
| 6,602,472 | B1 | 8/2003 | Zimmermann et al. |
| 6,620,625 | B2 | 9/2003 | Wolk et al. |
| 6,637,463 | B1 | 10/2003 | Lei et al. |
| 6,638,749 | B1 | 10/2003 | Beckman et al. |
| 6,660,367 | B1 | 12/2003 | Yang et al. |
| 6,663,619 | B2 | 12/2003 | Odrich et al. |
| 6,664,044 | B1 | 12/2003 | Sato |
| 6,670,153 | B2 | 12/2003 | Stern |
| 6,753,147 | B2 | 6/2004 | Vogelstein et al. |
| 6,767,706 | B2 | 7/2004 | Quake et al. |
| 6,773,566 | B2 | 8/2004 | Shenderov |
| 6,808,882 | B2 | 10/2004 | Griffiths et al. |
| 6,814,934 | B1 | 11/2004 | Higuchi |
| 6,833,242 | B2 | 12/2004 | Quake et al. |
| 6,900,021 | B1 | 5/2005 | Harrison et al. |
| 6,905,885 | B2 | 6/2005 | Colston et al. |
| 6,949,176 | B2 | 9/2005 | Vacca et al. |
| 6,960,437 | B2 | 11/2005 | Enzelberger et al. |
| 6,964,846 | B1 | 11/2005 | Shuber |
| 7,010,391 | B2 | 3/2006 | Handique et al. |
| 7,041,481 | B2 | 5/2006 | Anderson et al. |
| 7,052,244 | B2 | 5/2006 | Fouillet et al. |
| 7,081,336 | B2 | 7/2006 | Bao et al. |
| 7,091,048 | B2 | 8/2006 | Parce et al. |
| 7,094,379 | B2 | 8/2006 | Fouillet et al. |
| 7,118,910 | B2 | 10/2006 | Unger et al. |
| 7,129,091 | B2 | 10/2006 | Ismagilov et al. |
| 7,138,233 | B2 | 11/2006 | Griffiths et al. |
| 7,141,537 | B2 | 11/2006 | Audenaert et al. |
| 7,192,557 | B2 | 3/2007 | Wu et al. |
| 7,198,897 | B2 | 4/2007 | Wangh et al. |
| 7,238,268 | B2 | 7/2007 | Ramsey et al. |
| 7,244,567 | B2 | 7/2007 | Chen et al. |
| 7,252,943 | B2 | 8/2007 | Griffiths et al. |
| 7,268,167 | B2 | 9/2007 | Higuchi et al. |
| 7,268,179 | B2 | 9/2007 | Brown |
| 7,270,786 | B2 | 9/2007 | Parunak et al. |
| 7,279,146 | B2 | 10/2007 | Nassef et al. |
| 7,294,468 | B2 | 11/2007 | Bell et al. |
| 7,294,503 | B2 | 11/2007 | Quake et al. |
| 7,306,929 | B2 | 12/2007 | Ignatov et al. |
| 7,312,085 | B2 | 12/2007 | Chou et al. |
| 7,323,305 | B2 | 1/2008 | Leamon et al. |
| 7,368,233 | B2 | 5/2008 | Shuber et al. |
| 7,375,140 | B2 | 5/2008 | Higuchi et al. |
| 7,423,751 | B2 | 9/2008 | Hairston et al. |
| 7,429,467 | B2 | 9/2008 | Holliger et al. |
| 7,567,596 | B2 | 7/2009 | Dantus et al. |
| 7,579,172 | B2 | 8/2009 | Cho et al. |
| 7,595,195 | B2 | 9/2009 | Lee et al. |
| 7,622,280 | B2 | 11/2009 | Holliger et al. |
| 7,629,123 | B2 | 12/2009 | Millonig et al. |
| 7,776,927 | B2 | 8/2010 | Chu et al. |
| 7,807,920 | B2 | 10/2010 | Linke et al. |
| 7,842,457 | B2 | 11/2010 | Berka et al. |
| 8,399,198 | B2 | 3/2013 | Hiddessen et al. |
| 2001/0046701 | A1 | 11/2001 | Schulte et al. |
| 2002/0021866 | A1 | 2/2002 | Everett et al. |
| 2002/0022261 | A1 | 2/2002 | Anderson et al. |
| 2002/0060156 | A1 | 5/2002 | Mathies et al. |
| 2002/0068357 | A1 | 6/2002 | Mathies et al. |
| 2002/0093655 | A1 | 7/2002 | Everett et al. |
| 2002/0141903 | A1 | 10/2002 | Parunak et al. |
| 2002/0142483 | A1 | 10/2002 | Yao et al. |
| 2002/0151040 | A1 | 10/2002 | O'Keefe et al. |
| 2002/0164820 | A1 | 11/2002 | Brown |
| 2002/0195586 | A1 | 12/2002 | Auslander et al. |
| 2003/0001121 | A1 | 1/2003 | Hochstein |
| 2003/0003054 | A1 | 1/2003 | McDonald et al. |
| 2003/0003441 | A1 | 1/2003 | Colston et al. |
| 2003/0008308 | A1 | 1/2003 | Enzelberger et al. |
| 2003/0027150 | A1 | 2/2003 | Katz |
| 2003/0027244 | A1 | 2/2003 | Colston et al. |
| 2003/0027352 | A1 | 2/2003 | Hooper et al. |
| 2003/0032172 | A1 | 2/2003 | Colston, Jr. et al. |
| 2003/0049659 | A1 | 3/2003 | Lapidus et al. |
| 2003/0087300 | A1 | 5/2003 | Knapp et al. |
| 2003/0170698 | A1 | 9/2003 | Gascoyne et al. |
| 2003/0180765 | A1 | 9/2003 | Traverso et al. |
| 2003/0204130 | A1 | 10/2003 | Colston, Jr. et al. |
| 2004/0007463 | A1 | 1/2004 | Ramsey et al. |
| 2004/0038385 | A1 | 2/2004 | Langlois et al. |
| 2004/0067493 | A1 | 4/2004 | Matsuzaki et al. |
| 2004/0068019 | A1 | 4/2004 | Higuchi et al. |
| 2004/0074849 | A1 | 4/2004 | Brown et al. |
| 2004/0171055 | A1 | 9/2004 | Brown |
| 2004/0180346 | A1 | 9/2004 | Anderson et al. |
| 2004/0208792 | A1 | 10/2004 | Linton et al. |
| 2005/0036920 | A1 | 2/2005 | Gilbert |
| 2005/0042639 | A1 | 2/2005 | Knapp et al. |
| 2005/0064460 | A1 | 3/2005 | Holliger et al. |
| 2005/0079510 | A1 | 4/2005 | Berka et al. |
| 2005/0112541 | A1 | 5/2005 | Durack et al. |
| 2005/0172476 | A1 | 8/2005 | Stone et al. |
| 2005/0202429 | A1 | 9/2005 | Trau et al. |
| 2005/0221279 | A1 | 10/2005 | Carter et al. |

(56) References Cited

U.S. PATENT DOCUMENTS

2005/0221373 A1 10/2005 Enzelberger et al.
2005/0227264 A1 10/2005 Nobile et al.
2005/0239192 A1 10/2005 Nasarabadi et al.
2005/0277125 A1 12/2005 Benn et al.
2005/0282206 A1* 12/2005 Corbett et al. .................... 435/6
2006/0014187 A1 1/2006 Li et al.
2006/0057599 A1 3/2006 Dzenitis et al.
2006/0077755 A1 4/2006 Higuchi et al.
2006/0079583 A1 4/2006 Higuchi et al.
2006/0079584 A1 4/2006 Higuchi et al.
2006/0079585 A1 4/2006 Higuchi et al.
2006/0094108 A1 5/2006 Yoder et al.
2006/0106208 A1 5/2006 Nochumson et al.
2006/0188463 A1 8/2006 Kim et al.
2007/0003442 A1 1/2007 Link et al.
2007/0010974 A1 1/2007 Nicoli et al.
2007/0048756 A1 3/2007 Mei et al.
2007/0109542 A1 5/2007 Tracy et al.
2007/0166200 A1 7/2007 Zhou et al.
2007/0195127 A1 8/2007 Ahn et al.
2007/0196397 A1 8/2007 Torii et al.
2007/0202525 A1 8/2007 Quake et al.
2007/0231393 A1 10/2007 Ritter et al.
2007/0242111 A1 10/2007 Pamula et al.
2007/0248956 A1 10/2007 Buxbaum et al.
2007/0258083 A1 11/2007 Heppell et al.
2007/0275415 A1 11/2007 Srinivasan et al.
2008/0003142 A1 1/2008 Link et al.
2008/0014589 A1 1/2008 Link et al.
2008/0038810 A1 2/2008 Pollack et al.
2008/0070862 A1 3/2008 Laster et al.
2008/0090244 A1 4/2008 Knapp et al.
2008/0138815 A1 6/2008 Brown et al.
2008/0145923 A1 6/2008 Hahn et al.
2008/0153091 A1 6/2008 Brown et al.
2008/0160525 A1 7/2008 Brown et al.
2008/0161420 A1 7/2008 Shuber
2008/0166793 A1 7/2008 Beer et al.
2008/0169184 A1 7/2008 Brown et al.
2008/0169195 A1 7/2008 Jones et al.
2008/0171324 A1 7/2008 Brown et al.
2008/0171325 A1 7/2008 Brown et al.
2008/0171326 A1 7/2008 Brown et al.
2008/0171327 A1 7/2008 Brown et al.
2008/0171380 A1 7/2008 Brown et al.
2008/0171382 A1 7/2008 Brown et al.
2008/0213766 A1 9/2008 Brown et al.
2008/0214407 A1 9/2008 Remacle et al.
2008/0262384 A1 10/2008 Wiederkehr et al.
2008/0268436 A1 10/2008 Duan et al.
2008/0274455 A1 11/2008 Puskas et al.
2008/0280331 A1 11/2008 Davies et al.
2008/0280865 A1 11/2008 Tobita
2008/0280955 A1 11/2008 McCamish
2008/0314761 A1 12/2008 Herminghaus et al.
2009/0012187 A1 1/2009 Chu et al.
2009/0026082 A1 1/2009 Rothberg et al.
2009/0029867 A1 1/2009 Reed et al.
2009/0035770 A1 2/2009 Mathies et al.
2009/0035838 A1 2/2009 Quake et al.
2009/0061428 A1 3/2009 McBride et al.
2009/0068170 A1 3/2009 Weitz et al.
2009/0069194 A1 3/2009 Ramakrishnan
2009/0098044 A1 4/2009 Kong et al.
2009/0114043 A1 5/2009 Cox
2009/0131543 A1 5/2009 Weitz et al.
2009/0162929 A1 6/2009 Ikeda
2009/0176271 A1 7/2009 Durack et al.
2009/0203063 A1 8/2009 Wheeler et al.
2009/0217742 A1 9/2009 Chiu et al.
2009/0220434 A1 9/2009 Sharma
2009/0235990 A1 9/2009 Beer
2009/0239308 A1 9/2009 Dube et al.
2009/0291435 A1 11/2009 Unger et al.
2009/0311713 A1 12/2009 Pollack et al.
2009/0325184 A1 12/2009 Woudenberg et al.
2009/0325234 A1* 12/2009 Gregg et al. ................. 435/91.2
2009/0325236 A1 12/2009 Griffiths et al.
2010/0009360 A1 1/2010 Rosell Costa et al.
2010/0020565 A1 1/2010 Seward
2010/0022414 A1 1/2010 Link et al.
2010/0041046 A1 2/2010 Chiu et al.
2010/0047808 A1 2/2010 Reed et al.
2010/0069250 A1 3/2010 White, III et al.
2010/0069263 A1 3/2010 Shendure et al.
2010/0092973 A1 4/2010 Davies et al.
2010/0137163 A1 6/2010 Link et al.
2010/0173394 A1 7/2010 Colston, Jr. et al.
2010/0248385 A1 9/2010 Tan et al.
2010/0261229 A1 10/2010 Lau et al.
2010/0304446 A1 12/2010 Davies et al.
2010/0304978 A1 12/2010 Deng et al.
2011/0000560 A1 1/2011 Miller et al.
2011/0027394 A1 2/2011 McClements et al.
2011/0053798 A1 3/2011 Hindson et al.
2011/0070589 A1 3/2011 Belgrader et al.
2011/0086780 A1 4/2011 Colston, Jr. et al.
2011/0092373 A1 4/2011 Colston, Jr. et al.
2011/0092376 A1 4/2011 Colston, Jr. et al.
2011/0092392 A1 4/2011 Colston, Jr. et al.
2011/0118151 A1 5/2011 Eshoo et al.
2011/0160078 A1 6/2011 Fodor et al.
2011/0177563 A1 7/2011 Hahn et al.
2011/0183330 A1 7/2011 Lo et al.
2011/0217712 A1 9/2011 Hiddessen et al.
2011/0217736 A1 9/2011 Hindson
2011/0218123 A1 9/2011 Weitz et al.
2011/0244455 A1 10/2011 Larson et al.
2011/0250597 A1 10/2011 Larson et al.
2011/0311978 A1 12/2011 Makarewicz, Jr. et al.
2012/0021423 A1 1/2012 Colston, Jr. et al.
2012/0028311 A1 2/2012 Colston, Jr. et al.
2012/0122714 A1 5/2012 Samuels et al.
2012/0152369 A1 6/2012 Hiddessen et al.
2012/0171683 A1 7/2012 Ness et al.
2012/0190032 A1 7/2012 Ness et al.
2012/0190033 A1 7/2012 Ness et al.
2012/0194805 A1 8/2012 Ness et al.
2012/0208241 A1 8/2012 Link
2012/0219947 A1 8/2012 Yurkovetsky et al.
2012/0220494 A1 8/2012 Samuels et al.
2012/0264646 A1 10/2012 Link et al.
2012/0302448 A1 11/2012 Hutchison et al.
2012/0309002 A1 12/2012 Link
2012/0329664 A1 12/2012 Saxonov et al.
2013/0017551 A1 1/2013 Dube
2013/0040841 A1 2/2013 Saxonov et al.
2013/0045875 A1 2/2013 Saxonov et al.
2013/0059754 A1 3/2013 Tzonev
2013/0064776 A1 3/2013 El Harrak et al.
2013/0084572 A1 4/2013 Hindson et al.
2013/0099018 A1 4/2013 Miller et al.
2013/0109575 A1 5/2013 Kleinschmidt et al.

FOREIGN PATENT DOCUMENTS

GB 1 503 163 3/1978
GB 2 097 692 11/1982
JP 0295433 4/1990
WO 82/02562 8/1982
WO 84/02000 5/1984
WO 92/01812 2/1992
WO 94/05414 3/1994
WO 96/12194 4/1996
WO 98/00231 1/1998
WO WO9816313 A1 4/1998
WO 98/44151 10/1998
WO 98/44152 10/1998
WO 98/47003 10/1998
WO 01/07159 2/2001
WO 01/12327 2/2001
WO 02/23163 3/2002
WO 02/060584 8/2002
WO 02/068104 9/2002

(56) References Cited

FOREIGN PATENT DOCUMENTS

| | | | |
|---|---|---|---|
| WO | 02/081490 | | 10/2002 |
| WO | 02/081729 | | 10/2002 |
| WO | WO03016558 | A1 | 2/2003 |
| WO | 03/042410 | | 5/2003 |
| WO | 03/072258 | | 9/2003 |
| WO | 2004/040001 | | 5/2004 |
| WO | 2005/007812 | | 1/2005 |
| WO | 2005/010145 | | 2/2005 |
| WO | 2005/021151 | | 3/2005 |
| WO | 2005/023091 | | 3/2005 |
| WO | 2005/055807 | | 6/2005 |
| WO | 2005/073410 | | 8/2005 |
| WO | 2005/075683 | | 8/2005 |
| WO | 2006/023719 | | 3/2006 |
| WO | 2006/027757 | | 3/2006 |
| WO | 2006/038035 | | 4/2006 |
| WO | 2006/086777 | | 8/2006 |
| WO | 2006/095981 | | 9/2006 |
| WO | 2007/091228 | | 8/2007 |
| WO | 2007/091230 | | 8/2007 |
| WO | 2007/092473 | | 8/2007 |
| WO | 2007/133710 | | 11/2007 |
| WO | 2008/021123 | | 2/2008 |
| WO | 2008/024114 | | 2/2008 |
| WO | 2008/063227 | | 5/2008 |
| WO | 2008/070074 | | 6/2008 |
| WO | 2008/070862 | | 6/2008 |
| WO | 2008/109176 | | 9/2008 |
| WO | 2008/109878 | | 9/2008 |
| WO | 2008/112177 | | 9/2008 |
| WO | WO2009002920 | A1 | 12/2008 |
| WO | 2009/015863 | | 2/2009 |
| WO | 2009/049889 | | 4/2009 |
| WO | 2009/085246 | | 7/2009 |
| WO | 2010/001419 | | 1/2010 |
| WO | 2010/018465 | | 2/2010 |
| WO | 2011/034621 | | 3/2011 |
| WO | 2011/079176 | | 6/2011 |

OTHER PUBLICATIONS

Young, Lee W., Authorized officer, International Searching Authority, Written Opinion of the International Searching Authority, PCT Application Serial No. PCT/US2009/05317; mailing date: Nov. 20, 2009.

Beer et al., "On-Chip, Real-Time, Single-Copy Polymerase Chain Reaction in Picoliter Droplets", Analytical Chemistry, Nov. 15, 2007, vol. 79, No. 22, pp. 8471-8475.

Beer et al., "On-Chip Single-Copy Real-Time, Reverse-Transcription PCR in Isolated Picoliter Droplets", Analytical Chemistry, Mar. 15, 2008, vol. 80, No. 6, pp. 1854-1858.

J. Smid-Korbar et al., "Efficiency and usability of silicone surfactants in emulsions," International Journal of Cosmetic Science 12, pp. 135-139, (1990), presented at the 15$^{th}$ IFSCC International Congress, Sep. 26-29, 1988, London.

A. Chittofrati et al., "Perfluoropolyether microemulsions," Progress in Colloid & Polymer Science 79, pp. 218-225, (1989).

Steven A. Snow, "Synthesis and Characterization of Zwitterionic Silicone Sulfobetaine Surfactants," Langmuir, vol. 6, No. 2, American Chemical Society, pp. 385-391, (1990).

Polydimethylsiloxane, 5 pgs., published in FNP 52 (1992).

Russell Higuchi et al., "Kinetic PCR Analysis: Real-time Monitoring of DNA Amplification Reactions," Bio/Technology vol. II, pp. 1026-1030, Sep. 11, 1993.

D. A. Newman et al., "Phase Behavior of Fluoroether-Functional Amphiphiles in Supercritical Carbon Dioxide," The Journal of Supercritical Fluids, vol. 6, No. 4, pp. 205-210, (1993).

Y. Sela et al., "Newly designed polysiloxane-graft-poly (oxyethylene) copolymeric surfactants: preparation, surface activity and emulsification properties," Colloid & Polymer Science 272, pp. 684-691, (1994).

M. Gasperlin et al., "The structure elucidation of semisolid w/o emulsion systems containing silicone surfactant," International Journal of Pharmaceutics 107, pp. 51-56, (1994).

Mieczyslaw A. Piatyszek et al., "Detection of telomerase activity in human cells and tumors by a telomeric repeat amplification protocol (TRAP)," Methods in Cell Science 17, pp. 1-15, (1995).

Anthony P. Shuber et al., "A Simplified Procedure for Developing Multiplex PCRs," Genome Research, published by Cold Spring Harbor Laboratory Press, pp. 488-493, (1995).

A. V. Yazdi et al., "Highly Carbon Dioxide Soluble Surfactants, Dispersants and Chelating Agents," Fluid Phase Equilibria, vol. 117, pp. 297-303, (1996).

Ariel A. Avilion et al., "Human Telomerase RNA and Telomerase Activity in Immortal Cell Lines and Tumor Tissues," Cancer Research 56, pp. 645-650, Feb. 1, 1996.

Shuming Nie et al., "Optical Detection of Single Molecules," Annu. Rev. Biophys. BiomoL Struct. vol. 26, pp. 567-596, (1997).

Edith J. Singley et al., "Phase behavior and emulsion formation of novel fluoroether amphiphiles in carbon dioxide," Fluid Phase Equilibria 128, pp. 199-219, (1997).

Olga Kalinina et al., "Nanoliter scale PCR with TaqMan Detection," Nucleic Acids Research, vol. 25, No. 10 pp. 1999-2004, (1997).

Zhen Guo et al., "Enhanced discrimination of single nucleotide polymorphisms by artificial mismatch hybridization," Nature Biotechnology vol. 15, pp. 331-335, Apr. 1997.

E. G. Ghenciu et al., "Affinity Extraction into Carbon Dioxide. 1. Extraction of Avidin Using a Biotin-Functional Fluoroether Surfactant," Ind. Eng. Chem. Res. vol. 36, No. 12, pp. 5366-5370, Dec. 1, 1997.

Paschalis Alexandridis, Structural Polymorphism of Poly(ethylene oxide)-Poly(propylene oxide) Block Copolymers in Nonaqueous Polar Solvents, Macromolecules, vol. 31, No. 20, pp. 6935-6942, Sep. 12, 1998.

Sandro R. P. Da Rocha et al., "Effect of Surfactants on the Interfacial Tension and Emulsion Formation between Water and Carbon Dioxide," Langmuir, vol. 15, No. 2, pp. 419-428, (1999), published on web Dec. 29, 1998.

Bert Vogelstein et al., "Digital PCR," Proc. Natl. Acad. Sci. USA, vol. 96, pp. 9236-9241, Aug. 1999.

Anthony J. O'Lenick, Jr., "Silicone Emulsions and Surfactants," Journal of Surfactants and Detergents, vol. 3, No. 3, Jul. 2000.

N. Garti et al., "Water Solubilization in Nonionic Microemulsions Stabilized by Grafted Siliconic Emulsifiers," Journal of Colloid and Interface Science vol. 233, pp. 286-294, (2001).

Shinji Katsura et al., "Indirect micromanipulation of single molecules in water-in-oil emulsion," Electrophoresis, vol. 22, pp. 289-293, (2001).

Hironobu Kunieda et al., "Effect of Hydrophilic- and Hydrophobic-Chain Lengths on the Phase Behavior of A-B-type Silicone Surfactants in Water," J. Phys. Chem. B, vol. 105, No. 23, pp. 5419-5426, (2001).

Hidenori Nagai et al., "Development of a Microchamber Array for Picoliter PCR," Analytical Chemistry, vol. 73, No. 5, pp. 1043-1047, Mar. 1, 2001.

Christopher B. Price, "Regular Review Point of Care Testing," BMJ, vol. 322, May 26, 2001.

3M Specialty Materials, "3M Fluorinert Electronic Liquid FC-3283," product information guide, issued Aug. 2001.

Ivonne Schneegaβ et al., "Miniaturized flow-through PCR with different template types in a silicon chip thermocycler," Lab on a Chip, vol. 1, pp. 42-49, (2001).

Randla M. Hill, "Silicone surfactants—new developments," Current Opinion in Colloid & Interface Science 7, pp. 255-261, (2002).

Richard M. Cawthon, "Telomere measurement by quantitative PCR," Nucleic Acids Research, vol. 30, No. 10, pp. 1-6, (2002).

Anfeng Wang et al., "Direct Force Measurement of Silicone- and Hydrocarbon-Based ABA Triblock Surfactants in Alcoholic Media by Atomic Force Mircroscopy," Journal of Colloid and Interface Science 256, pp. 331-340 (2002).

Shelley L. Anna et al., "Formation of dispersions using "flow focusing" in microchannels," Applied Physics Letters, vol. 82, No. 3, Jan. 20, 2003.

(56) References Cited

OTHER PUBLICATIONS

Goldschmidt GMBH, "Abil® EM 90 Emulsifier for the formulation of cosmetic W/O creams and lotions," degussa. creating essentials brochure, pp. 1-7, May 2003.
Purnendu K. Dasgupta et al., "Light emitting diode-based detectors Absorbance, fluorescence and spectroelectrochemical measurements in a planar flow-through cell," Analytica Chimica Acta 500, pp. 337-364, (2003).
R. G. Rutledge et al., "Mathematics of quantitative kinetic PCR and the application of standard curves," Nucleic Acids Research, vol. 31, No. 16, pp. 1-6, (2003).
Chunming Ding et al., "Direct molecular haplotyping of long-range genomic DNA with M1-PCR," PNAS, vol. 100, No. 13, pp. 7449-7453, Jun. 24, 2003.
Devin Dressman et al., "Transforming single DNA molecules into fluorescent magnetic particles for detection and enumeration of genetic variations," PNAS, vol. 100, No. 15, Jul. 22, 2003.
Ulf Landegren et al., "Padlock and proximity probes for in situ and array-based analyses: tools for the post-genomic era," Comp. Funct. Genom, vol. 4, pp. 525-530, (2003).
Gudrun Pohl et al., "Principle and applications of digital PCR" review, www.future-drugs.com, Expert Rev. Mol. Diagn. 4(1), pp. 41-47, (2004).
Groff M. Schroeder et al., "Introduction to Flow Cytometry" version 5.1, 182 pgs. (2004).
Stéphane Swillens et al., "Instant evaluation of the absolute initial number of cDNA from a single real-time PCR curve," Nucleic Acids Research, vol. 32, No. 6, pp. 1-6, (2004).
Mats Gullberg et al., "Cytokine detection by antibody-based proximity ligation," PNAS, vol. 101, No. 22, pp. 8420-8424, Jun. 1, 2004.
Tianhao Zhang et al., "Behavioral Modeling and Performance Evaluation of Microelectrofluidics-Based PCR Systems Using SystemC," IEEE Transactions on Computer-Aided Design of Integrated Circuits and Systems, vol. 23, No. 6, pp. 843-858, Jun. 2004.
R. G. Rutledge, "Sigmoidal curve-fitting redefines quantitative real-time PCR with the prospective of developing automated high-throughput applications," Nucleic Acids Research. vol. 32, No. 22, pp. 1-8, (2004).
L. Spencer Roach et al., "Controlling Nonspecific Protein Absorption in a Plug-Based Microfluidic System by Controlling Interfacial Chemistry Using Fluorous-Phase Surfactants," Analytical Chemistry vol. 77, No. 3, pp. 785-796, Feb. 1, 2005.
Kevin D. Dorfman et al., "Contamination-Free Continuous Flow Microfluidic Polymerase Chain Reaction for Quantitative and Clinical Applications," Analytical Chemistry vol. 77, No. 11, pp. 3700-3704, Jun. 1, 2005.
James G. Wetmur et al., "Molecular haplotyping by linking emulsion PCR: analysis of paraoxonase 1 haplotypes and phenotypes," Nucleic Acids Research, vol. 33, No. 8, pp. 2615-2619, (2005).
Piotr Garstecki et al., "Mechanism for Flow-Rate Controlled Breakup in Confined Geometries: A Route to Monodisperse Emulsions," Physical Review Letters, 164501, pp. 164501-1-164501-4, Apr. 29, 2005.
Anna Musyanovych et al., "Miniemulsion Droplets as Single Molecule Nanoreactors for Polymerase Chain Reaction," Biomacromolecules, vol. 6, No. 4, pp. 1824-1828, (2005).
Max Chabert et al., "Droplet fusion by alternating current (AC) field electrocoalescence in microchannels," Electrophoresis, vol. 26, pp. 3706-3715, (2005).
Takaaki Kojima et al., "PCR amplification from single DNA molecules on magnetic beads in emulsion: application for high-throughput screening of transcription factor targets," Nucleic Acids Research, vol. 33, No. 17, pp. 1-9, (2005).
Marcel Margulies et al., "Genome sequencing in microfabricated high-density picolitre reactors," Nature, vol. 437, 51 pgs., Sep. 15, 2005.
Kristofer J. Thurecht et al., "Investigation of spontaneous microemulsion formation in supercritical carbon dioxide using high-pressure NMR," Journal of Supercritical Fluids, vol. 38, pp. 111-118, (2006).
Toshko Zhelev et al., "Heat Integration in Micro-Fluidic Devices," $16^{th}$ European Symposium on Computer Aided Process Engineering and $9^{th}$ International Symposium on Process Systems Engineering, pp. 1863-1868 published by Elsevier B.V. (2006).
Piotr Garstecki et al., "Formation of droplets and bubbles in a microfluidic T-junction—scaling and mechanism of break-up," Lab on a Chip, vol. 6, pp. 437-446, (2006).
Darren R. Link et al., "Electric Control of Droplets in Microfluidic Devices," Angewandte Chemie Int. Ed., vol. 45, pp. 2556-2560, (2006).
Peter Fielden et al., "Micro-Droplet Technology for High Throughout Systems and Methods," 1 pg., Mar. 8, 2006.
David Emerson et al., "Microfluidic Modelling Activities at C3M," Centre for Microfluidics & Microsystems Modelling, Daresbury Laboratory, pp. 1-26, May 15, 2006.
Richard Williams et al., "Amplification of complex gene libraries by emulsion PCR," Nature Methods, vol. 3, No. 7, pp. 545-550, Jul. 2006.
John H. Leamon et al., "Overview: methods and applications for droplet compartmentalization of biology," Nature Methods, vol. 3, No. 7, pp. 541-543, Jul. 2006.
Andrew D. Griffiths et al., "Miniaturising the laboratory in emulsion droplets," TRENDS in Biotechnology, vol. 24, No. 9, pp. 395-402, Jul. 14, 2006.
Jian-Bing Fan et al., "Highly parallel genomic assays," Nature Reviews/Genetics, vol. 7, pp. 632-644, Aug. 2006.
Jonas Jarvius et al., "Digital quantification using amplified single-molecule detection," Nature Methods, vol. 3, No. 9, pp. 15 pgs, Sep. 2006.
Kan Liu et al., "Droplet-based synthetic method using microflow focusing and droplet fusion," Microfluid Nanfluid, vol. 3, pp. 239-243, (2007), published online Sep. 22, 2006.
Dimitris Glotsos et al., "Robust Estimation of Bioaffinity Assay Fluorescence Signals," IEEE Transactions on Information Technology in Biomedicine, vol. 10, No. 4, pp. 733-739, Oct. 2006.
Kristofer J. Thurecht et al., "Kinetics of Enzymatic Ring-Opening Polymerization of ϵ-Caprolactone in Supercritical Carbon Dioxide," Macromolecules, vol. 39, pp. 7967-7972, (2006).
Machiko Hori et al., "Uniform amplification of multiple DNAs by emulsion PCR," Biochemical and Biophysical Research Communications, vol. 352, pp. 323-328, (2007).
Frank Diehl et al., "Digital quantification of mutant DNA in cancer patients," Current Opinion in Oncology, vol. 19, pp. 36-42, (2007).
Delai L. Chen et al., "Using Three-Phase Flow of Immiscible Liquids to Prevent Coalescence of Droplets in Microfluidic Channels: Criteria to Identify the Third Liquid and Validation with Protein Crystallization," Langmuir, vol. 23, No. 4, pp. 2255-2260, (2007).
S. Mohr et al., "Numerical and experimental study of a droplet-based PCR chip," Microfluid Nanofluid, vol. 3, pp. 611-621, (2007).
Sigrun M. Gustafsdottir et al., "In vitro analysis of DNA-protein interactions by proximity ligation," PNAS, vol. 104, No. 9, pp. 3067-3072, Feb. 27, 2007.
Daniel J. Diekema et al., "Look before You Leap: Active Surveillance for Multidrug-Resistant Organisms," Healthcare Epidemiology • CID 2007:44, pp. 1101-1107 (Apr. 15), electronically published Mar. 2, 2007.
Charles N. Baroud et al., "Thermocapillary valve for droplet production and sorting," Physical Review E 75, 046302, pp. 046302-1-046302-5, Apr. 5, 2007.
Qinyu Ge et al., "Emulsion PCR-based method to detect Y chromosome microdeletions," Analytical Biochemistry, vol. 367, pp. 173-178, May 10, 2007.
Chunsun Zhang et al., "Miniaturized PCR chips for nucleic acid amplification and analysis: latest advances and future trends," Nucleic Acids Research, vol. 35, No. 13, pp. 4223-4237, Jun. 18, 2007.
Y. M. Dennis Lo et al., "Digital PCR for the molecular detection of fetal chromosomal aneuploidy," PNAS, vol. 104, No. 32, pp. 13116-13121, Aug. 7, 2007.
Dayong Jin et al., "Practical Time-Gated Luminescence Flow Cytometry. II: Experimental Evaluation Using UV LED Excitation," Cytometry Part A • 71A, pp. 797-808, Aug. 24, 2007.

(56) References Cited

OTHER PUBLICATIONS

Helen R. Hobbs et al., "Homogeneous Biocatalysis in both Fluorous Biphasic and Supercritical Carbon Dioxide Systems," Angewandte Chemie, vol. 119, pp. 8006-8009, Sep. 6, 2007.

Nathan Blow, "PCR's next frontier," Nature Methods, vol. 4, No. 10, pp. 869-875, Oct. 2007.

Nicole Pamme, "continuous flow separations in microfluidic devices," Lab on a Chip, vol. 7, pp. 1644-1659, Nov. 2, 2007.

Yuejun Zhao et al., "Microparticle Concentration and Separation by Traveling-Wave Dielectrophoresis (twDEP) for Digital Microfluidics," Journal of Microelectromechanical Systems, vol. 16, No. 6, pp. 1472-1481, Dec. 2007.

Sigma-Aldrich, "Synthesis of Mesoporous Materials," Material Matters, 3.1, 17, (2008).

Nick J. Carroll et al., "Droplet-Based Microfluidics for Emulsion and Solvent Evaporation Synthesis of Monodisperse Mesoporous Silica Microspheres," Langmuir, vol. 24, No. 3, pp. 658-661, Jan. 3, 2008.

Shia-Yen Teh et al., "Droplet microfluidics," Lab on a Chip, vol. 8, pp. 198-220, Jan. 11, 2008.

Chloroform (Phenomenex), Solvent Miscibility Table, Internet Archive WayBackMachine, 3 pgs., Feb. 1, 2008.

Palani Kumaresan et al., "High-Throughput Single Copy DNA Amplification and Cell Analysis in Engineered Nanoliter Droplets," Analytical Chemistry, 17 pgs., Apr. 15, 2008.

Somil C. Mehta et a., "Mechanism of Stabilization of Silicone Oil—Water Emulsions Using Hybrid Siloxane Polymers," Langmuir, vol. 24, No. 9, pp. 4558-4563, Mar. 26, 2008.

Rhutesh K. Shah et al., "Polymers fit for function Making emulsions drop by drop," Materials Today, vol. 11, No. 4, pp. 18-27, Apr. 2008.

Mohamed Abdelgawad et al., "All-terrain droplet actuation," Lab on a Chip, vol. 8, pp. 672-677, Apr. 2, 2008.

Lung-Hsin Hung et al., "Rapid microfabrication of solvent-resistant biocompatible microfluidic devices," Lab on a Chip, vol. 8, pp. 983-987, Apr. 8, 2008.

Jenifer Clausell-Tormos et al., "Droplet-Based Microfluidic Platforms for the Encapsulation and Screening of Mammalian Cells and Multicellular Organisms," Chemistry & Biology, vol. 15, pp. 427-437, May 2008.

Vivienne N. Luk et al., "Pluronic Additives: A Solution to Sticky Problems in Digital Microfluidics," Langmuir, vol. 24, No. 12, pp. 6382-6289, May 16, 2008.

Yen-Heng Lin et al., "Droplet Formation Utilizing Controllable Moving-Wall Structures for Double-Emulsion Applications," Journal of Microelectromechanical Systems, vol. 17, No. 3, pp. 573-581, Jun. 2008.

Simant Dube et al., "Mathematical Analysis of Copy Number Variation in a DNA Sample Using Digital PCR on a Nanofluidic Device," PLoS ONE, vol. 3, Issue 8, pp. 1-9, Aug. 6, 2008.

Jian Qin et al., "Studying copy number variations using a nanofluidic platform," Nucleic Acids Research, vol. 36, No. 18, pp. 1-8, Aug. 18, 2008.

C. Holtze et al., "Biocompatible surfactants for water-in-fluorocarbon emulsions," Lab on a Chip, vol. 8, pp. 1632-1639, Sep. 2, 2008.

Margaret Macris Kiss et al., "High-Throughput Quantitative Polymerase Chain Reaction in Picoliter Droplets," Analytical Chemistry, 8 pgs., downloaded Nov. 17, 2008.

Jay Shendure et al., "Next-generation DNA sequencing," Nature Biotechnology, vol. 26, No. 10, pp. 1135-1145, Oct. 2008.

Bernhard G. Zimmermann et al., "Digital PCR: a powerful new tool for noninvasive prenatal diagnosis?," Prenatal Diagnosis, vol. 28 pp. 1087-1093, Nov. 10, 2008.

Avishay Bransky et al., "A microfluidic droplet generator based on a piezoelectric actuator," Lab on a Chip, vol. 9, pp. 516-520, Nov. 20, 2008.

David A. Weitz, "Novel Surfactants for Stabilizing Emulsions of Water or Hydrocarbon Oil-Based Droplets in a Fluorocarbon Oil Continuous Phase," Harvard Office of Technology Development: Available Technologies, pp. 1-3, downloaded Nov. 28, 2008.

Neil Reginald Beer et al., "Monodisperse droplet generation and rapid trapping for single molecule detection and reaction kinetics measurement," Lab on a Chip, vol. 9, pp. 841-844, Dec. 5, 2008.

Richard M. Cawthon, "Telomere length measurement by a novel monochrome multiplex quantitative PCR method," Nucleic Acids Research, vol. 37, No. 3, pp. 1-7, (2009).

Anthony J. O'Lenick, Jr., "Silicone Emulsions and Surfactants—A Review," Silicone Spectator, Silitech LLC, May 2009 (original published May 2000).

Adam R. Abate et al., "Functionalized glass coating for PDMS microfluidic devices," Lab on a Chip Technology: Fabrication and Microfluidics, 11 pgs., (2009).

Chia-Hung Chen et al., "Janus Particles Templated from Double Emulsion Droplets Generated Using Microfluidics," Langmuir, vol. 29, No. 8, pp. 4320-4323, Mar. 18, 2009.

Luis M. Fidalgo et al., "Coupling Microdroplet Microreactors with Mass Spectrometry: Reading the Contents of Single Droplets Online," Angewandte Chemie, vol. 48, pp. 3665-3668, Apr. 7, 2009.

Linas Mazutis et al., "A fast and efficient microfluidic system for highly selective one-to-one droplet fusion," Lab on a Chip, vol. 9, pp. 2665-2672, Jun. 12, 2009.

Linas Mazutis et al., "Droplet-Based Microfluidic Systems for High-Throughput Single DNA Molecule Isothermal Amplification and Analysis," Analytical Chemistry, vol. 81, No. 12, pp. 4813-4821, Jun. 15, 2009.

Frank McCaughan et al., "Single-molecule genomics," Journal of Pathology, vol. 220, pp. 297-306, Nov. 19, 2009.

Suzanne Weaver et al., "Taking qPCR to a higher level: Analysis of CNV reveals the power of high throughput qPCR to enhance quantitative resolution," Methods, vol. 50, pp. 271-276, Jan. 15, 2010.

Amelia L. Markey et al., "High-throughput droplet PCR," Methods, vol. 50, pp. 277-281, Feb. 2, 2010.

Yoon Sung Nam et al., "Nanosized Emulsions Stabilized by Semisolid Polymer Interphase," Langmuir, ACS Publications, Jul. 23, 2010.

Tatjana Schütze et al., "A streamlined protocol for emulsion polymerase chain reaction and subsequent purification," Analytical Biochemistry, vol. 410, pp. 155-157, Nov. 25, 2010.

Somanath Bhat et al., "Effect of sustained elevated temperature prior to amplification on template copy number estimation using digital polymerase chain reaction," Analyst, vol. 136, pp. 724-732, (2011).

James G. Wetmur, et al., "Linking Emulsion PCR Haplotype Analysis," PCR Protocols, Methods in Molecular Biology, vol. 687, pp. 165-175, (2011).

Paul Vulto et al., "Phaseguides: a paradigm shift in microfluidic priming and emptying," Lab on a Chip, vol. 11, No. 9, pp. 1561-1700, May 7, 2011.

Thinxxs Microtechnology AG, "Emerald Biosystems: Protein Crystallization," 1 pg., downloaded Mar. 8, 2011.

Qun Zhong et al., "Multiplex digital PCR: breaking the one target per color barrier of quantitative PCR," Lab on a Chip, vol. 11, pp. 2167-2174, (2011).

Jiaqi Huang et al., "Rapid Screening of Complex DNA Samples by Single-Molecule Amplification and Sequencing," PLoS ONE, vol. 6, Issue 5, pp. 1-4, May 2011.

Burcu Kekevi et al., Synthesis and Characterization of Silicone-Based Surfactants as Anti-Foaming Agents, J. Surfact Deterg (2012), vol. 15, pp. 73-81, published online Jul. 7, 2011.

Leonardo B. Pinheiro et al., "Evaluation of a Droplet Digital Polymerase Chain Reaction Format for DNA Copy Number Quantification," Analytical Chemistry, vol. 84, pp. 1003-1011, Nov. 28, 2011.

Nicole L. Solimini et al., "Recurrent Hemizygous Deletions in Cancers May Optimize Proliferative Potential," Science, vol. 337, pp. 104-109, Jul. 6, 2012.

Labsmith, "Microfluid Components" webpage, downloaded Jul. 11, 2012.

Labsmith, "CapTite™ Microfluidic Interconnects" webpage, downloaded Jul. 11, 2012.

(56) References Cited

OTHER PUBLICATIONS

Nathan A. Tanner et al., "Simultaneous multiple target detection in real-time loop-mediated isothermal amplification," BioTechniques, vol. 53, pp. 8-19, Aug. 2012.

A. Scherer, California Institute of Technology, "Polymerase Chain Reactors" PowerPoint presentation, 24 pgs., date unknown.

Eschenback Optik GMBH, Optics for Concentrated Photovoltaics (CPV), 1 pg., date unknown.

* cited by examiner

FLOW-BASED THERMOCYCLING SYSTEM WITH THERMOELECTRIC COOLER

CROSS-REFERENCES TO PRIORITY APPLICATIONS

This application is a continuation-in-part of U.S. patent application Ser. No. 12/586,626, filed Sep. 23, 2009.

U.S. patent application Ser. No. 12/586,626, in turn, is based upon and claims the benefit under 35 U.S.C. §119(e) of the following U.S. provisional patent applications: Ser. No. 61/194,043, filed Sep. 23, 2008; Ser. No. 61/206,975, filed Feb. 5, 2009; Ser. No. 61/271,538, filed Jul. 21, 2009; Ser. No. 61/275,731, filed Sep. 1, 2009; Ser. No. 61/277,200, filed Sep. 21, 2009; Ser. No. 61/277,203, filed Sep. 21, 2009; Ser. No. 61/277,204, filed Sep. 21, 2009; Ser. No. 61/277,216, filed Sep. 21, 2009; Ser. No. 61/277,249, filed Sep. 21, 2009; and Ser. No. 61/277,270, filed Sep. 22, 2009.

Each of these patent applications is incorporated herein by reference in its entirety for all purposes.

CROSS-REFERENCES TO ADDITIONAL MATERIALS

This application incorporates herein by reference U.S. Pat. No. 7,041,481, issued May 9, 2006, in its entirety for all purposes.

INTRODUCTION

Assays may be used to detect the presence and characteristics of certain nucleic acids in a sample. Nucleic acids are molecules found inside cells, organelles, and viruses. Nucleic acids, such as deoxyribonucleic acid (DNA) and ribonucleic acid (RNA), contain the unique blueprint, or genes, of each biological entity. Drug discovery, genetic analysis, pharmacogenomics, clinical diagnostics, and general biomedical research all use assays for nucleic acids. The most widely used assay for DNA analysis involves first amplifying a target DNA and then detecting the amplified target DNA with the use of a fluorescent dye. The most common amplification technique used today is the polymerase chain reaction (PCR).

PCR, which was developed in 1983, enables a single strand of nucleic acid to be amplified over a million times. The completion of the Human Genome Project, a 13-year effort by the U.S. Department of Energy and the National Institutes of Health to identify all of the approximately 20,000-25,000 genes in human DNA and to determine the sequence of the three billion chemical base pairs that make up human DNA, as well as the exponentially decreasing cost of sequencing, currently is spawning many new applications for this technology.

Real-time PCR (rtPCR) is a variant of PCR that involves monitoring a sample while DNA amplification is occurring. The benefit of this real-time capability is that it enables a practitioner to determine the amount of a target sequence of interest that was present initially in the sample before the amplification by PCR. The basic objective of rtPCR is to distinguish and measure precisely the amount of one or more specific nucleic acid target sequences in a sample, even if there is only a very small number of corresponding target molecules. rtPCR amplifies a specific target sequence in a sample and then monitors the amplification progress using fluorescence technology. During amplification, the speed with which the fluorescence signal reaches a threshold level correlates with the amount of original target sequence, thereby enabling quantification. However, the accuracy of this measurement is limited, because it relies on determining the point at which the fluorescence signal becomes exponential. Because most samples are complex (containing many different DNAs), because amplification efficiency can be extremely variable, and because a single cycle represents a doubling of the amount of nucleic acid target, typical measurement values can vary by as much as two- to four-fold or more. Moreover, reaction times for current rtPCR instruments are fundamentally limited by the use of relatively large sample volumes and the thermal mass of reaction vessels.

DNA amplification, such as via PCR, relies on temperature-dependent reactions for increasing the number of copies of a sample, or component(s) thereof. In particular, in a process termed thermocycling, a fluid is cyclically heated and cooled, which may be accomplished with an apparatus, a "thermocycler," which produces such cyclical temperature variations. In the case of DNA amplification through PCR, cyclical temperature changes cause repeated denaturation (also sometimes termed DNA "melting"), primer annealing, and polymerase extension of the DNA undergoing amplification. Typically, thirty to forty cycles or more are performed to obtain detectable amplification.

FIG. 1 shows a flowchart depicting a method, generally indicated at 100, of thermocycling a fluid mixture to promote PCR. Typically, three separate temperatures or temperature ranges are provided to the fluid to accomplish thermocycling for PCR. In the case of PCR, providing a first, relatively higher temperature to the fluid, as indicated at step 102, causes the target DNA to become denatured. Providing a second, relatively lower temperature to the fluid, as indicated at step 104, allows annealing of DNA primers to the single-stranded DNA templates that result from denaturing the original double-stranded DNA. Finally, providing a third, middle temperature to the fluid, as indicated at step 106, allows a DNA polymerase to synthesize a new, complementary DNA strand starting from the annealed primer.

In some cases, a single temperature may be provided for both primer annealing and polymerase extension (i.e., steps 104 and 106 above), although providing a single temperature for these processes may not optimize the activity of the primers and/or the polymerase, and thus may not optimize the speed of the PCR reaction. When provided for both annealing and extension, this single temperature is typically in the range of 55-75° C.

Various methods of providing the desired temperatures or temperature ranges to a sample/reagent fluid mixture may be suitable for PCR. For example, a fluid may be disposed within one or more stationary fluid sites, such as test tubes, microplate wells, PCR plate wells, or the like, which can be subjected to various temperatures provided in a cyclical manner by an oven or some other suitable heater acting on the entire thermal chamber. However, such array-type PCR systems may be limited by the number of fluid sites that can practically be fluidically connected to the system. Also, these array-type PCR systems may be limited by the kinetics of changing temperatures in a large (high-thermal-mass) system. For example, transition times between melt, anneal, and extension temperatures in commercial systems may be orders of magnitude longer than the fundamental limits of Taq polymerase processivity.

Thus, there is a need for new systems for thermocycling samples.

SUMMARY

The present disclosure provides a thermocycling system, including methods and apparatus, for performing a flow-based reaction on a sample in fluid. The system may include a plurality of segments defining at least two temperature regions, and also may include a plurality of heating elements configured to maintain each temperature region at a different desired temperature. At least one of the heating elements may be a thermoelectric cooler operatively disposed to transfer heat to and/or from a temperature region The system further may include a fluid channel extending along a helical path that passes through the temperature regions multiple times such that fluid flowing in the channel is heated and cooled cyclically.

DETAILED DESCRIPTION

Figure 1:
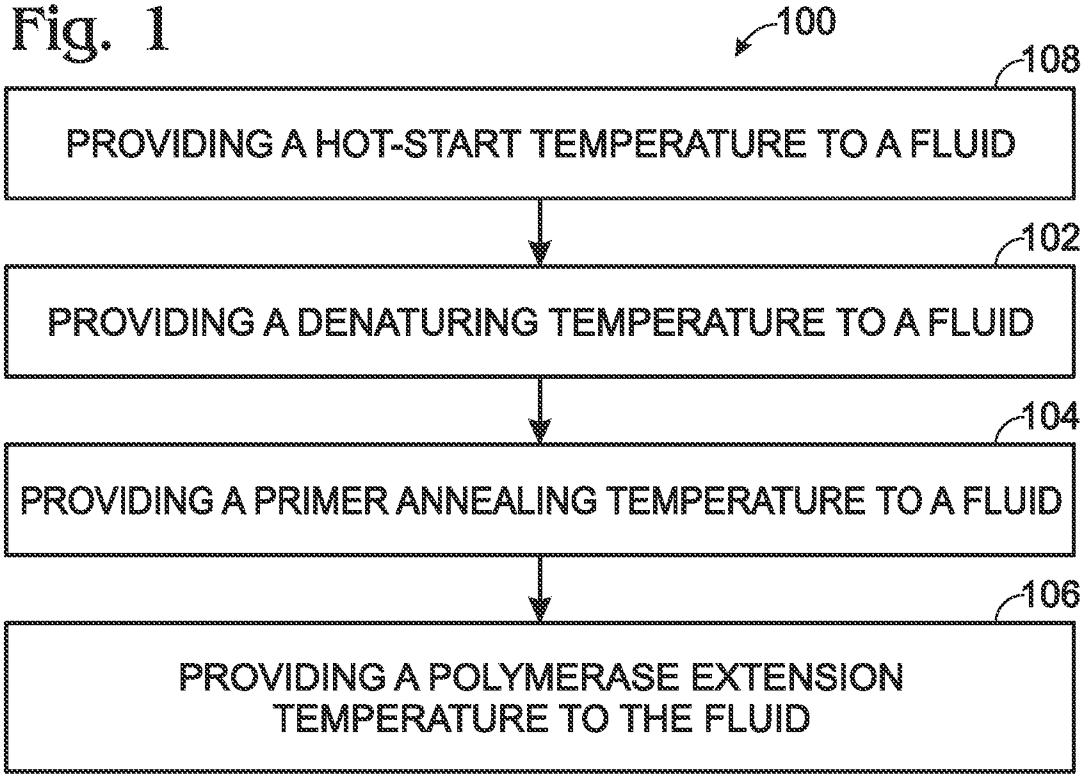
FIG. 1 is a flowchart depicting a method of thermocycling a sample/reagent fluid mixture to promote PCR.

The present disclosure provides a thermocycling system, including methods and apparatus, for performing a flow-based reaction on a sample in fluid. The system may include a plurality of segments defining at least two temperature regions, and also may include a plurality of heating elements configured to maintain each temperature region at a different desired temperature. The system further may include a fluid channel extending along a path, such as a helical or planar path, that passes through the temperature regions multiple times such that fluid flowing in the channel is heated and cooled cyclically. The present disclosure emphasizes, but it not limited to, a flow-based thermocycling system for amplifying a sample, such as a nucleic-acid sample, particularly for use in droplet-based assays.

The system, in some embodiments, may incorporate a thermoelectric cooler (TEC) as a heating element. The TEC may be operatively disposed to transfer heat to and/or from at least one temperature region. For example, the TEC may be operatively disposed to transfer heat between a pair of the temperature regions and/or to transfer heat between a temperature region and a body member (e.g., a core) configured as a heat source and/or a heat sink. In some cases, distinct thermoelectric coolers may be operatively disposed to transfer heat between the body member and each respective temperature region. The utilization of at least one thermoelectric cooler may improve the speed and precision with which the desired temperature of a temperature region can be attained or adjusted, the efficiency with which the desired temperature can be maintained, and/or the response of the system to varying thermal loads, among others.

The system, in some embodiments, may have at least one temperature region that varies in size along a central axis of the helical path. The central axis also or alternatively may be defined by the body member, the segments collectively, or a combination thereof. The fluid channel may have a different path length for successive passes through at least one temperature region, thereby changing how much time the fluid spends in the temperature region during each of the successive passes, if the fluid travels along the fluid channel at a uniform speed. The utilization of a temperature region that varies in size may permit the temperature profile and/or duration of each heating/cooling cycle to be tailored more closely to changing demands of the thermocycling reaction at different cycle numbers, among others.

The system, in some embodiments, may have a varying number of temperature regions along a central axis of the helical path. For example, the fluid channel may extend through a plurality of revolutions about the central axis, and the number of temperature regions per revolution may vary. The utilization of a varying number of temperature regions may, for example, permit samples to be prepared by heating them in the fluid channel before thermocycling, thermocycled with varying thermal profiles during the course of a thermocycling operation, and/or processed after thermocycling, among others.

A flow-based reaction on a sample in fluid may be performed. A plurality of segments defining at least two temperature regions may be provided. A plurality of heating elements may be operated to maintain each temperature region at a different desired temperature. Fluid and/or droplets may be transported in a fluid channel extending along a path, such as a helical or planar path, that passes through the temperature regions multiple times such that fluid (and/or droplets) flowing in the fluid channel is heated and cooled cyclically. In some embodiments, the fluid (and/or droplets) may be heated and cooled cyclically for a plurality of cycles and each having a duration. The duration of each of two or more of the cycles at a beginning of the plurality of cycles may be longer than the duration of each remaining cycle. In some embodiments, the plurality of heating elements may include a thermoelectric cooler that is operated to transfer heat to and/or from a temperature region. In some embodiments, the step of transporting droplets may be performed with the droplets disposed in a carrier fluid and positioned upstream, downstream, or both upstream and downstream of a barrier fluid that forms a moving barrier to droplet dispersion along the fluid channel.

These and other aspects of the present disclosure are described in the following sections: (I) exemplary thermocycling systems, (II) exemplary flow-based thermocycler, and (III) examples.

I. Exemplary Thermocycling Systems

This section describes an overview of selected aspects of the thermocycling systems disclosed herein; see FIG. 1.

FIG. 1 shows a flowchart depicting a method, generally indicated at 100, of thermocycling a sample/reagent emulsion or other fluid mixture to promote PCR. Typically, three separate temperatures or temperature ranges are provided to the fluid to accomplish thermocycling for PCR. Other numbers of temperature ranges, such as one, two, four, or more, may be provided for different amplification strategies and/or other flow-based processes. In the case of PCR, providing a first, relatively higher temperature to the fluid, as indicated at step 102, causes the target DNA to become denatured. This denaturing temperature is typically in the range of 92-98° C. Providing a second, relatively lower temperature to the fluid, as indicated at step 104, allows annealing of DNA primers to the single-stranded DNA templates that result from denaturing the original double-stranded DNA. This primer annealing temperature is typically in the range of 50-65° C. Finally, providing a third, middle temperature to the fluid, as indicated at step 106, allows a DNA polymerase to synthesize a new, complementary DNA strand starting from the annealed primer. This polymerase extension temperature is typically in the range of 70-80° C., to achieve optimum polymerase activity, and depends on the type of DNA polymerase used.

Typically, when thermocycling reactions are performed on small sample volumes, such as droplets in an emulsion, about twenty or more cycles may be performed to obtain detectable amplification. In other processes, such as alternative enzymatic amplification processes, thermocycling may have other effects, and different temperature ranges and/or different numbers of temperature changes may be appropriate.

A PCR thermocycler, as disclosed herein, may include the two or three temperature regions or zones described above, and also may include an integrated or complementary "hot-start" mechanism configured to provide a relatively high hot-start temperature, as indicated at step 108. The hot-start temperature is provided to initiate PCR and/or to prepare a sample/reagent mixture for initiation of PCR upon the addition of a suitable polymerase. More specifically, providing a hot-start temperature may reverse the inhibition of a polymerase enzyme that has been added in an inactive configuration to inhibit priming events that might otherwise occur at room temperature. In this case, heating the sample/reagent mixture to a hot-start temperature initiates the onset of PCR. In other instances, providing a hot-start temperature may preheat the sample and the primers in the absence of the polymerase, in which case subsequent addition of the polymerase will initiate PCR. The hot start temperature is typically in the range of 95-98° C.

The thermocycler also may include integrated or complementary mechanisms for allowing "final elongation" and/or "final hold" steps, after thermocycling has (nominally) been completed. For example, in the former case, the thermocycler may include a mechanism configured to maintain samples at the extension temperature long enough (e.g., for 5-15 minutes) to ensure that any remaining single-stranded nucleotide is fully extended. In the flow-based systems disclosed herein, this mechanism may include a relatively long piece of narrow tubing to increase path length, and/or a relatively short piece of wider tubing to decrease flow rate, both maintained at an extension temperature. Alternatively, or in addition, the thermocycler may include a mechanism for holding or storing samples (e.g., for an indefinite time) at a temperature below the extension temperature (e.g., 4-15° C.).

The thermocycler disclosed herein is flow-based, meaning that fluid may be passed continuously or quasi-continuously through various temperature regions, in a cyclical manner. It may be desirable to minimize heat transfer between the temperature regions, to provide sharp temperature transitions between the regions. It also may be desirable to monitor the temperature of each region continuously and to provide rapid feedback to maintain a relatively constant desired temperature in each region.

The flow-based thermocycler may include a fluid channel that extends along a helical path which passes through the temperature regions multiple times. As a result, fluid flowing in the fluid channel is heated and cooled cyclically. The helical path may have a constant pitch or variable pitch. Accordingly, coils of the fluid channel may be uniformly spaced or may have a variable spacing. Alternatively, or in addition, the helical path may have a constant or variable diameter. If the helical path has a variable diameter, the diameter may vary stepwise or gradually/continuously. In some embodiments, the thermocycler may include a plurality of discrete fluid channels, each extending also a same helical path or extending along distinct helical paths. The discrete fluid channels may be addressable independently with fluid and/or droplets.

In some embodiments, the flow-based thermocycler involves coiling or winding fluidic tubing to form a fluid channel in a helical shape around a thermocycler that is configured to provide the various desired temperatures or temperature regions. Furthermore, various alternatives to externally wrapped fluidic tubing may be used to provide a fluid channel configured to transport fluid, such as an emulsion of sample-containing droplets, cyclically through various temperature regions. For example, tubing may be disposed within the body of thermocycler, such as by casting the thermocycler (or the inner segments of the thermocycler) around the tubing. Alternatively, a fluid tight coating (such as a silicon coating) may be applied to external grooves or channels of the thermocycler and then wrapped with a fluid tight sheet (such as a silicon sheet), to define an integrated fluid channel passing cyclically around the thermocycler without the need for any separate tubing at all.

Thus, providing the first, second, third and/or hot-start temperatures at steps 102, 104, 106, 108 of method 100 may include transporting an emulsion or other fluid mixture in a substantially helical path cyclically through a denaturing temperature region, a primer annealing temperature region, a polymerase extension temperature region, and/or a hot-start temperature region of the thermocycler. These various temperature regions may be thermally insulated from each other in various ways, and each region may provide a desired temperature through the use of resistive heating elements, thermoelectric coolers (TECs) configured to transfer heat between a thermal core and the temperature regions, and/or by any other suitable mechanism. Various heat sinks and sources may be used to provide and/or remove heat from the thermocycler, either globally (i.e., in substantial thermal contact with two or more temperature regions) or locally (i.e., in substantial thermal contact with only one temperature region).

The following examples describe specific exemplary methods and apparatus for cyclically heating and cooling a sample/reagent mixture to facilitate DNA amplification through PCR, i.e., exemplary thermocyclers and methods of thermocycling suitable for PCR applications. Additional pertinent disclosure may be found in the patent and patent applications listed above under Cross-references and incorporated herein by reference, particularly U.S. Pat. No. 7,041,481, issued May 9, 2006; U.S. Provisional Patent Application Ser. No. 61/194,043, filed Sep. 23, 2008; U.S. Provisional Patent Application Ser. No. 61/206,975, filed Feb. 5, 2009; U.S. Provisional Patent Application Ser. No. 61/277,200, filed Sep. 21, 2009; and U.S. patent application Ser. No. 12/586,626, filed Sep. 23, 2009.

II. Exemplary Flow-Based Thermocycler

This section describes an exemplary embodiment of a flow-based thermocycler 3200, in accordance with aspects of the present disclosure; see FIGS. 2-9.

Figure 2:
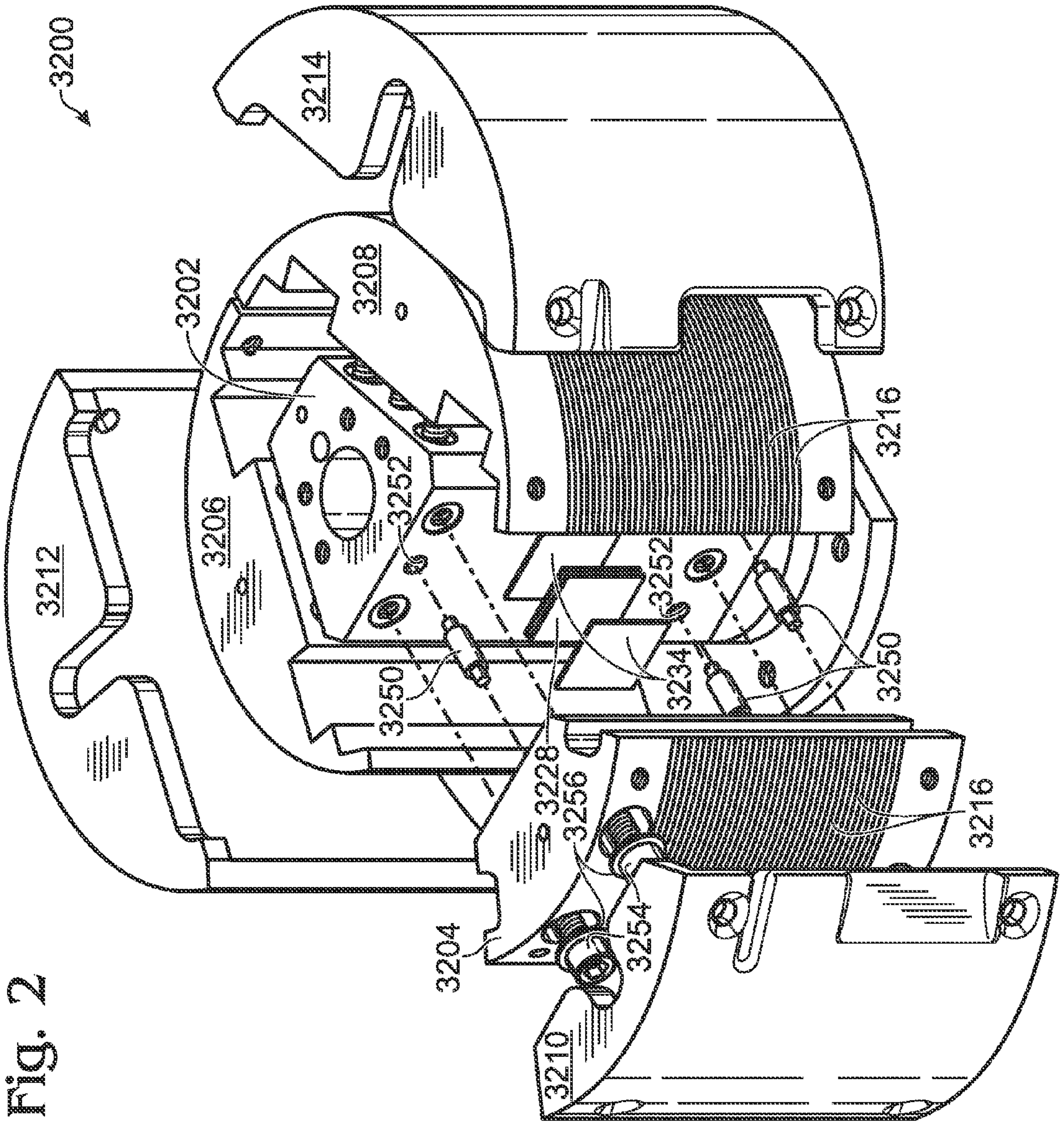
FIG. 2 is an exploded isometric view of an exemplary thermocycler, in accordance with aspects of the present disclosure.

FIG. 2 is an exploded isometric view of key components of thermocycler 3200. The thermocycler includes a core 3202 defining a central longitudinal axis, three inner segments 3204, 3206, 3208, and three outer segments 3210, 3212, 3214. The three pairs of segments correspond to the three portions of the PCR thermal cycle described above, in connection with FIG. 1, and define the corresponding temperature regions. Specifically, segments 3204 and 3210 correspond to the melt phase, segments 3206 and 3212 correspond to the anneal phase, and segments 3208 and 3214 correspond to the extension (extend) phase, respectively. In alternative embodiments, the thermocycler could include alternative numbers of segments, for example, two segments in a thermocycler in which the annealing and extension phases were combined. Collectively, portions or regions of the thermocycler involved in maintaining particular temperatures (or temperature ranges) may be termed "temperature regions" or "temperature-controlled zones," among other descriptions.

Figure 3:
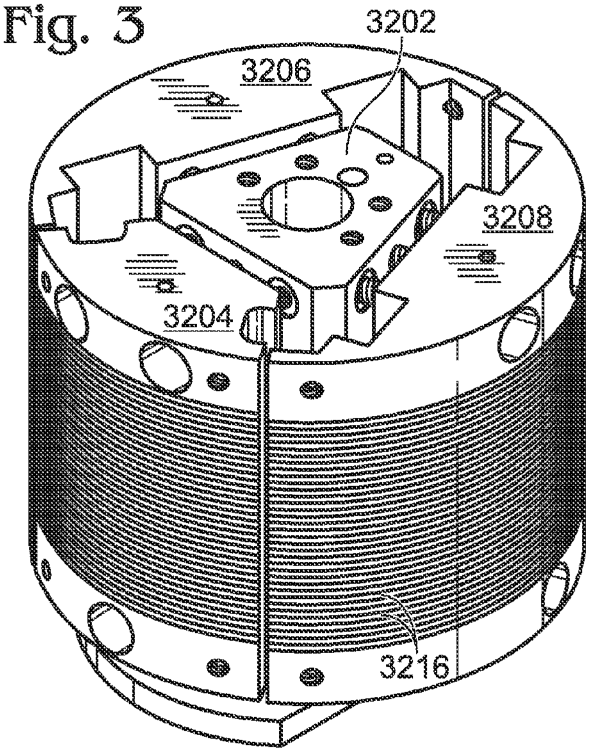
FIG. 3 is an unexploded isometric view of a central portion of the thermocycler of FIG. 2.

FIG. 3 is an unexploded isometric view of a central portion of the thermocycler of FIG. 2, emphasizing the relationship between the core and inner segments. Core 3202 is configured as both a heat source and a heat sink, which can be maintained at a constant desired temperature regardless of whether it is called upon to supply or absorb heat. For example, in some embodiments, core 3202 may be maintained at approximately 70 degrees Celsius. However, more generally, in embodiments in which the core acts as a heat source and a heat sink between two or more segments, the core may be maintained at any suitable temperature between the temperatures of the warmest and coolest segments (e.g., between the temperature of the melt segment and the annealing segment).

The thermocycler may include at least one body member that is a heat source, a heat sink, or both. The body member, such as core 3202, may be generally central to the segments considered collectively. For example, the segments may collectively define an opening and the body member may be disposed (at least partially) in the opening. Alternatively, or in addition, the segments collectively may define a central axis and at least a majority of the body member may be disposed farther from the central axis than the segments. The body member may define an opening and the segments may be disposed (at least partially) in the opening. The body member may (or may not) be coaxial with the segments considered collectively.

Inner segments 3204, 3206, 3208 are attached to the core and configured to form an approximate cylinder when all of the inner segments are attached or assembled to the core. Inner segments 3204, 3206, 3208 are equipped with external grooves 3216 on their outer peripheral surfaces, as visible in FIGS. 2 and 3. When the inner segments are assembled to the core, these grooves form a helical pattern around the circumference of the cylindrical surface formed by the inner segments. Grooves 3216 are configured to receive fluidic tubing that can be wrapped continuously around the inner segments, as described below, to allow a fluid traveling within the tubing to travel helically around the circumference formed by the assembled inner segments. The fluidic tubing acts as a fluid channel to transport an emulsion of sample-containing droplets cyclically through the various temperature regions of the thermocycling system.

Outer segments 3210, 3212, 3214 are configured to fit closely around the inner segments, as seen in FIG. 2. Thus, the fluidic tubing may be wound between the inner and outer segments and held in a stable, fixed, environmentally controlled position by the segments.

Figure 4:
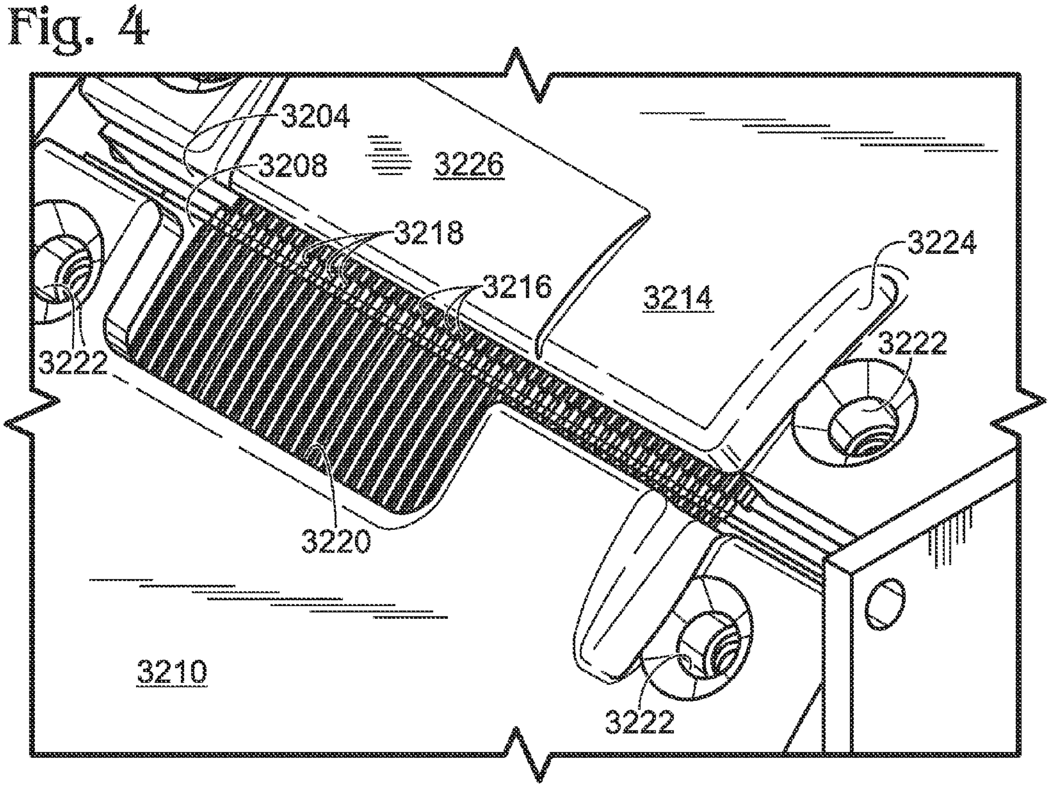
FIG. 4 is an isometric view showing a magnified portion of the assembled thermocycler of FIG. 2, which is suitable for relatively small outer diameter fluidic tubing, in accordance with aspects of the present disclosure.

FIG. 4 is an isometric magnified view of a portion of the assembled thermocycler. This embodiment is particularly suitable for relatively small outer diameter fluidic tubing. Portions of outer segments 3210, 3214 are disposed around inner segments 3204, 3208 and core 3202 (not visible). Fluidic tubing 3218 can be seen disposed in grooves 3216, which are partially visible within an aperture 3220 formed by the outer segments. Additional fastening apertures 3222 are provided in the outer segments to facilitate attachment of the outer segments to the inner segments. The tubing may pass from outside to inside thermocycler 3200 through an ingress region 3224. The tubing is then wrapped helically around the inner segments a minimum number of times, such as 20 or more times, after which the tubing may pass from inside to outside thermocycler 3200 through an egress region 3226. Egress region 3226 is relatively wide, to allow the tubing to exit thermocycler 3200 after forming any desired number of coils around the inner segments.

Figure 5:
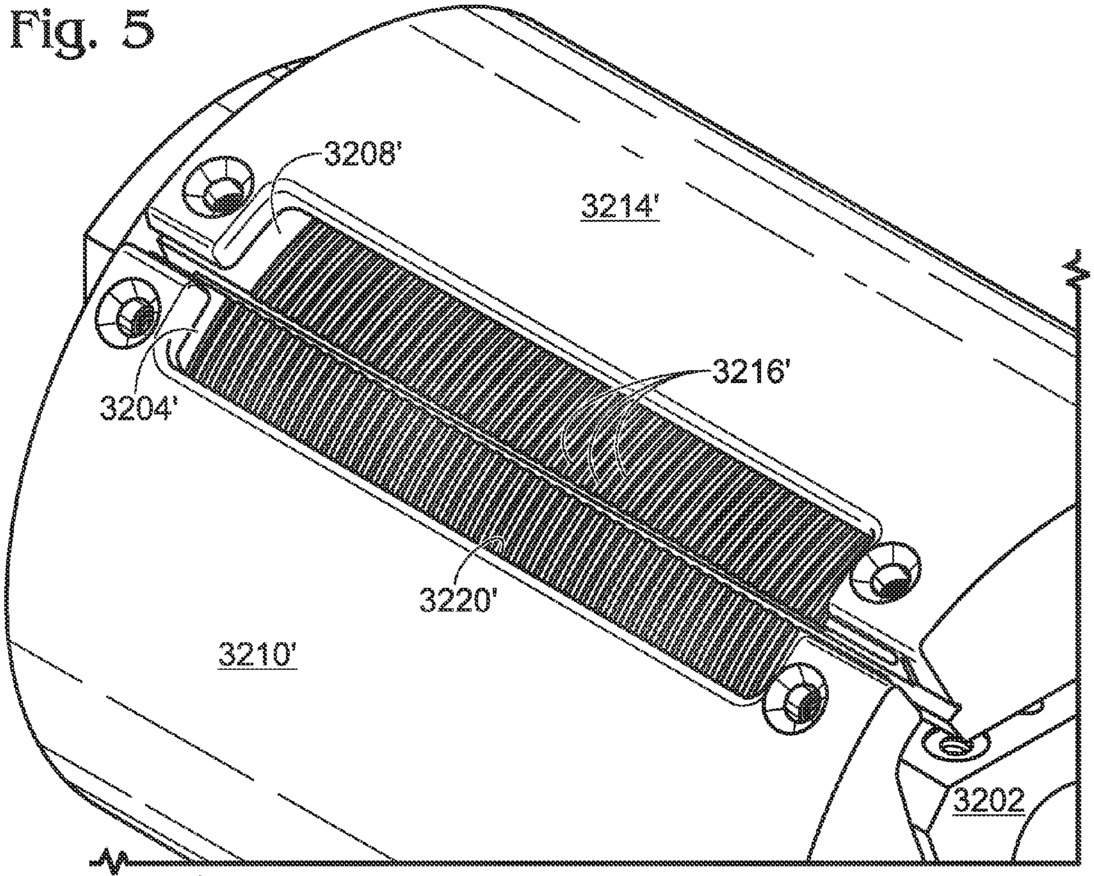
FIG. 5 is an isometric view showing a magnified portion of an alternative embodiment of the assembled thermocycler, which is suitable for relatively larger outer diameter fluidic tubing, in accordance with aspects of the present disclosure.

FIG. 5 is an isometric magnified view of a portion of an alternative embodiment of the assembled thermocycler. This embodiment, which shows a slight variation in the shape of the outer segments, is particularly suitable for relatively large outer diameter fluidic tubing. Specifically, FIG. 5 shows outer segments 3210, 3214 disposed around inner segments 3204, 3208 and core 3202. Grooves 3216, which are relatively wider than grooves 3216 of FIG. 4, are partially visible within an aperture 3220 formed by the outer segments. In FIG. 5, fluidic tubing may pass from outside to inside thermocycler 3200 and vice versa at any desired groove positions, simply by overlapping the edge of aperture 3220 with the tubing. Between the ingress and egress tubing positions, the tubing may be wrapped around the inner segments to make any desired number of helical coils around the inner segments.

Figure 6:
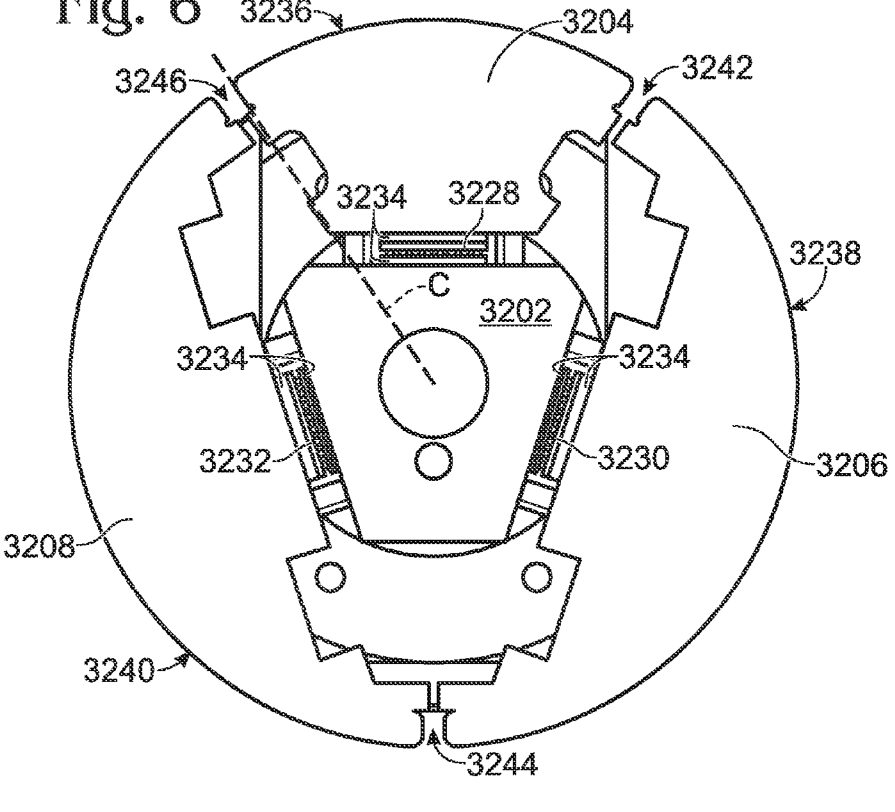
FIG. 6 is a top plan view of the thermocycler of FIG. 2, without the outer segments attached.

FIG. 6 is a top plan view of the assembled thermocycler, without the outer segments attached. This view shows three thermoelectric coolers (TECs) 3228, 3230, 3232 disposed between core 3202 and inner segments 3204, 3206, 3208. One of these, TEC 3228, can be seen in FIG. 2. Each TEC is configured to act as a heat pump, to maintain a desired temperature at its outer surface when a voltage is applied across the TEC. The TECs may be set to steady-state temperatures using a suitable controller, such as a proportional-integral-derivative (PID) controller, among others. The TECs operate according to well-known thermoelectric principles (in which, for example, current flow is coupled with heat transfer), such as the Peltier effect, the Seebeck effect, and/or the Thomson effect. The TECs may be configured to transfer heat in either direction (i.e., to or from a specific thermocycler element), with or against a temperature gradient, for example, by reversing current flow through the TEC. Thus, the TECs may be used to speed up or enhance heating of an element intended to be warm, speed up or enhance cooling of an element intended to be cool, and so on, to maintain each temperature region approximately at a different desired temperature. Suitable TECs include TECs available from RMT Ltd. of Moscow, Russia.

Each TEC, in turn, may be sandwiched between a pair of thermally conductive and mechanically compliant pads 3234, as seen in FIGS. 2 and 6. Pads 3234 may be configured to protect the TECs from damage due to surface irregularities on the outer surface of core 3202 and in the inner surfaces of inner segments 3204, 3206, 3208. Alternatively, or in addition, pads 3234 may be configured to minimize the possibility of potentially detrimental shear stresses on the TECs. Suitable pads include fiberglass-reinforced gap pads available from the Bergquist Company of Chanhassen, Minn.

Figure 7:
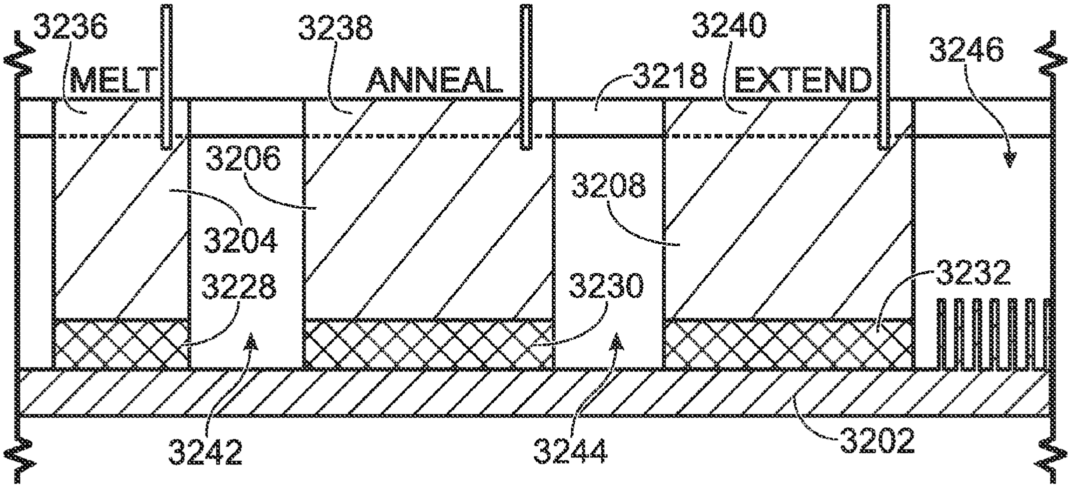
FIG. 7 is a schematic sectional view of the thermocycler of FIG. 2, depicting the relative dispositions of the core and other components, taken generally along line C in FIG. 6 as line C is swept through one clockwise revolution about the center of the thermocycler.

FIG. 7 is a schematic section diagram depicting the relative disposition of core 3202, TECs 3228, 3230, 3232, inner segments 3204, 3206, 3208, and tubing 3218. Here, the core, TECs, and inner segments are collectively configured to maintain the outer surfaces 3236, 3238, 3240, respectively, of the inner segments at any desired temperatures to facilitate PCR reactions in fluids passing through tubing disposed helically around the cylindrical perimeter of the assembled inner segments. FIG. 7 can be thought of as the top view shown in FIG. 6, cut along line C in FIG. 6 and shown “unrolled” into a representative linear configuration. FIG. 7 can be obtained from FIG. 6 by continuous deformation, making these figures topologically equivalent (homeomorphic), and meaning that FIG. 7 may simply be viewed as an alternate way of visualizing the arrangement of components shown in FIG. 6.

TECs 3228, 3230, and 3232 are configured to maintain outer surfaces 3236, 3238, 3240, respectively, of the inner segments at various temperatures corresponding to the different stages of PCR, as depicted in FIG. 7. Because tubing 3218 is in thermal contact with outer surfaces 3236, 3238, 3240, the temperature of any fluid in tubing 3218 also may be controlled via the TECs. Specifically, outer surface 3236 is maintained at a temperature $T_{melt}$ suitable for melting (or denaturing) DNA, outer surface 3238 is maintained at a temperature $T_{anneal}$ suitable for annealing primers to single-stranded DNA templates, and outer surface 3240 is maintained at a temperature $T_{extend}$ suitable for synthesizing new complementary DNA strands using a DNA polymerase.

TECs 3228, 3230, 3232 respond relatively rapidly to electrical signals and are independently controllable, so that the desired temperatures at outer surfaces 3236, 3238, 3240 may be maintained relatively accurately. This may be facilitated by temperature sensors that monitor the temperatures of the outer surfaces and provide real-time feedback signals to the TECs. Maintaining the various temperatures is also facilitated by gaps 3242, 3244, 3246, which are visible in both FIG. 6 and FIG. 7, between the inner segments. These gaps, which in this example are filled simply with air, provide insulation between the neighboring inner segments to help keep the inner segments thermally well-isolated from each other. In other embodiments, the gaps may be filled with other materials.

Figure 8:
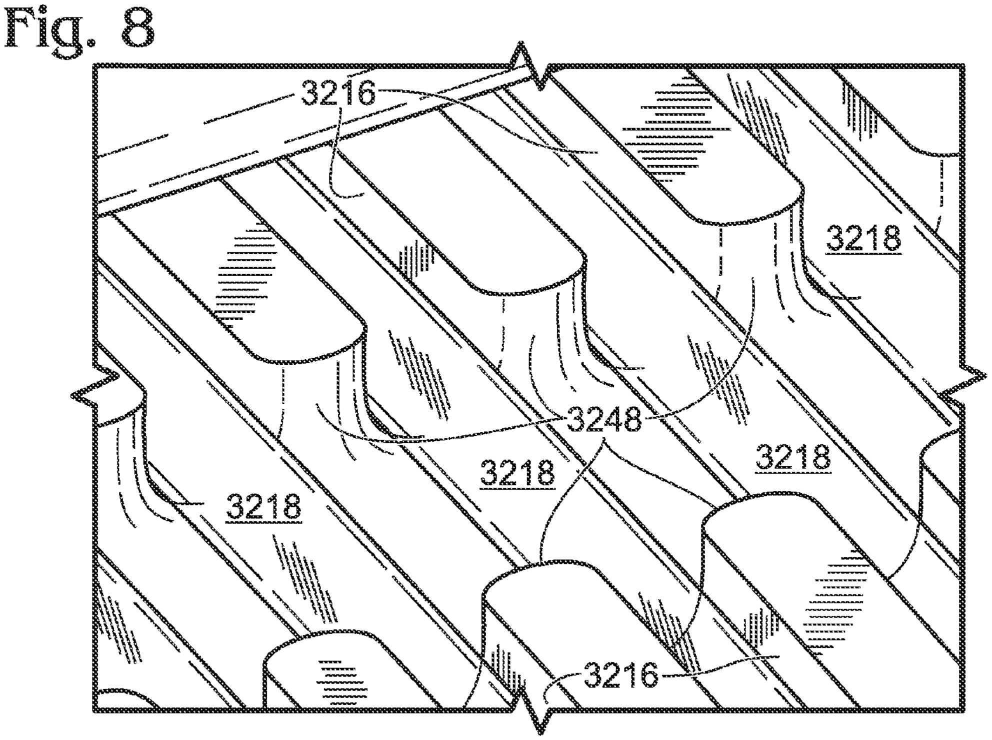
FIG. 8 is a magnified isometric view of a central portion of the thermocycler of FIG. 4.

FIG. 8 is a magnified isometric view of a central portion of grooves 3216 and tubing 3218 of FIG. 4, spanning the interface between two of the inner segments of the thermocycler. The features of the grooves shown in FIG. 8 are also present in grooves 3216 of FIG. 5. Specifically, grooves 3216 and 3216 include sloping edge contours 3248 disposed at the periphery of each inner segment 3204, 3206, 3208. Edge contours 3248 allow the tubing to be wrapped around the inner segments, even if there is a slight misalignment of two of the inner segments with respect to each other, because the edge contours do not include sharp edges that can be fracture points for tubing under stress from curvature due to potential misalignment.

The configuration of the inner segments in this example provides that each inner segment 3204, 3206, 3208 is substantially thermally decoupled from the other inner segments, as FIG. 7 illustrates schematically. This has advantages over systems in which the various temperature regions are in greater thermal contact, because in this exemplary configuration there is relatively little heat conduction between segments. One source of conduction that still exists is conduction via the fluid and fluidic tubing that passes from one inner segment to the next; however, as described below, the effects of this conduction on temperature uniformity are generally small.

Figure 9:
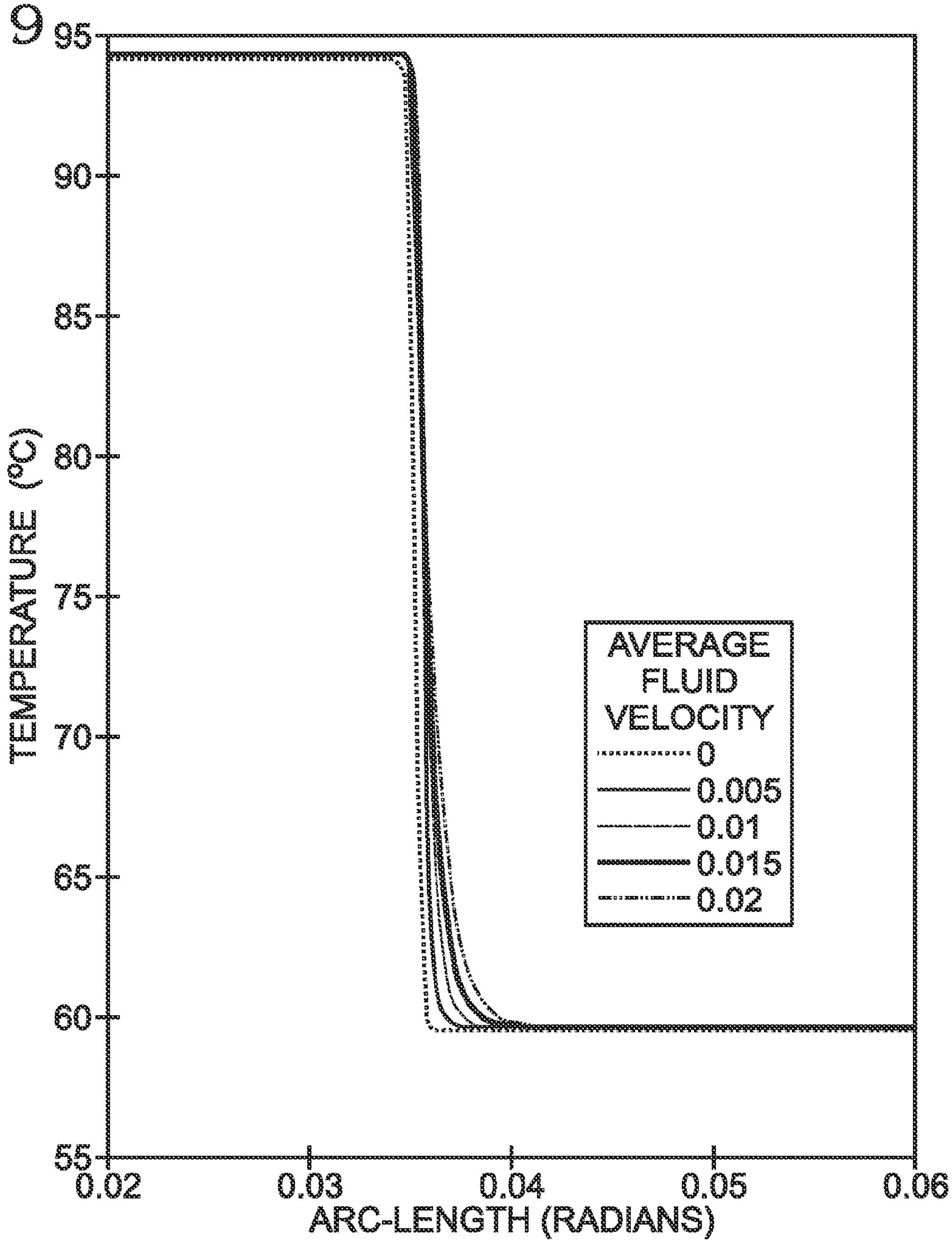
FIG. 9 is a graph of measured temperature versus arc length, as a function of average fluid velocity, near the interface between two inner segments of the thermocycler of FIG. 2.

FIG. 9 shows actual measured temperature versus arc length, as a function of average fluid velocity, near the interface between two inner segments configured according to this example. In particular, the effects of fluid heat conduction on temperature uniformity generally become insignificantly small within a few one-thousandths of a radian from the interface between inner segments, even for relatively rapid fluid velocity. Thus, the use TECs, in combination with closely spaced segments that are insulated from one another by air and/or another insulating material, may provide temperature changes that are substantially a step function, as illustrated for one step in FIG. 9. For example, angular travel of less than about 0.01 radians around a central axis of the helical path may separate adjacent temperature regions of different, substantially uniform temperature. Furthermore, TECs may be particularly advantageous over other heating configurations without TECs, because TECs generally provide faster equilibration in response to changes in thermal loads.

Cycle times (i.e., cycle durations) in the system generally are determined by the travel time for passage of fluid through the temperature regions. The travel times may be adjusted, through either hardware or software modifications, by changing (a) the fluid flow rate and/or (b) the length and/or volume of the flow path through the temperature regions.

The flow rate, as expressed by fluid volume per unit time, may be adjusted by changing one or more pump settings, such that fluid is pumped faster or slower through the temperature regions, to respectively decrease or increase cycle durations. In some cases, the flow rate alternatively or additionally may be adjusted by introducing additional fluid into the fluid channel at a position intermediate to the inlet and outlet of the fluid channel, after the fluid channel has extended through one or more thermal cycles. For example, additional fluid may be added at a channel intersection, such as a T-junction or a cross, such that fluid upstream of the intersection flows more slowly (for a longer cycle duration), and fluid downstream of the intersection flows more quickly (for a shorter cycle duration).

The length and/or volume of the flow path through the temperature regions may change, stepwise or gradually (or a combination thereof), as the fluid channel extends through successive thermal cycles. The length of the flow path may, for example, be changed by varying the diameter of the helical path as the fluid channel extends through successive cycles. The diameter may be varied stepwise or continuously (e.g., see Example 4). Changes to the diameter of the helical path may be produced by varying the drum radius, the arc length of one or more or each segment (since length of time in a given segment is proportional to the arc length of that segment), or the like. Alternatively, or in addition, the diameter of the fluid channel (e.g., the internal diameter of a capillary that forms the fluid channel) may vary, either stepwise or gradually/continuously. For example, the diameter of the fluid channel may be relatively wider (e.g., closer to the inlet), to produce relatively longer cycles time, and then may decrease to be relatively narrower (e.g., closer to the outlet), to provide relatively shorter cycle times.

Changing the cycle duration during the course of a reaction may be beneficial, such as when the earlier cycles are more critical than the later cycles. In this case, two or more earlier cycles (e.g., at least four or five cycles, among others) may have longer durations, to improve the accuracy and/or efficiency of the reaction, and subsequent cycles (e.g., at least eight or ten cycles, among others) may have shorter durations, to reduce the overall time to perform the reaction. The cycles may be performed in order, with the longer cycles performed at the beginning of the order, and each shorter cycle performed for the rest of the order. Also, the shorter cycles may outnumber the longer cycles. The longer cycles may, for example, have durations that are at least about 25%, 50%, 75%, or 100% longer than the shorter cycles. Further aspects of varying cycle durations during a reaction and an exemplary rationale therefor are presented in Example 4.

FIGS. 2 and 6 each show aspects of a mounting system for TECs 3228, 3230, 3232. Here, one TEC is mounted between core 3202 and each of inner segments 3204, 3206, 3208, as described previously. To attain positional accuracy when attaching each inner segment to the core, locating pins 3250 are configured to attach to both the core and one of the inner segments, to align each segment precisely with the core. Furthermore, the presence of the locating pins should reduce the likelihood that shear forces will act on the TECs and potentially damage them. The locating pins fit into complementary pin apertures 3252 disposed in both the inner segments and the core. In the exemplary embodiment of FIG. 2, a single locating pin is positioned at one end of the core (the top end in FIG. 2), and two locating pins are positioned at the other end of the core (the bottom end in FIG. 2).

FIG. 2 also shows bolts 3254 and washers 3256 configured to attach the inner segments to the core. The bolts are generally chosen to have low thermal conductivity, so that the TECs remain the only significant heat conduction path between the core and the inner segments. For instance, the bolts may be constructed from a heat-resistant plastic or a relatively low thermal conductivity metal to avoid undesirable thermal conduction. The washers may be load compensation washers, such as Belville-type washers, which are configured to provide a known compressive force that clamps each inner segment to the core. This bolt/washer combination resists loosening over time and also allows application of a known stress to both the bolts and the TECs, leading to greater longevity of the thermocycler.

III. Examples

The following examples describe selected aspects and embodiments of the present disclosure, particularly exemplary embodiments of flow-based thermocyclers.

These examples are included for illustration and are not intended to limit or define the entire scope of the invention.

Example 1

Exemplary Flow-Based Thermocycler with Hot-Start Region

Figure 10:
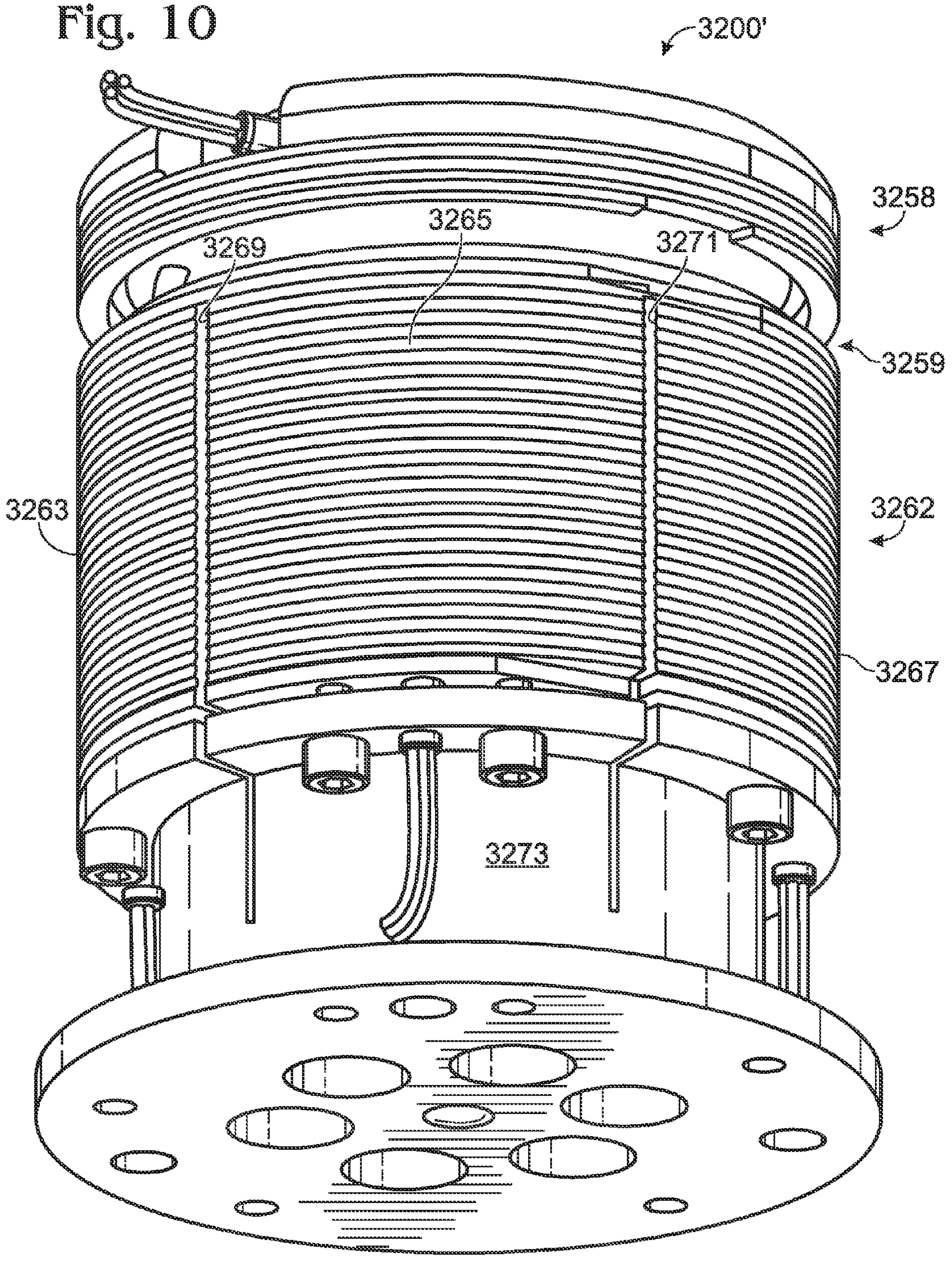
FIG. 10 is an isometric view of a central portion of a thermocycler having an optional "hot start" region, in accordance with aspects of the present disclosure.

This example describes an exemplary thermocycler 3200 containing a hot-start region, in accordance with aspects of the present disclosure; see FIG. 10.

Various modifications and/or additions may be made to the exemplary embodiments of FIGS. 2-9 according to the present disclosure. For example, a "hot start" mechanism may be added to facilitate a high-temperature PCR activation step. FIG. 10 shows a central portion (i.e., outer segments not shown) of an exemplary thermocycler 3200 including a hot start region 3258, which is separated from the remainder of the thermocycler by a gap 3259. The hot start region, like the inner segments, is configured to accept fluidic tubing, but is separated from the inner segments by gap 3259 to avoid unwanted heat conduction between the hot start region and the other portions of the thermocycler. A separate core portion (not shown) may be configured to heat region 3258 to a relatively high activation temperature, typically in the range of 95-98° C., to dissociate any polymerase inhibitors that have been used to reduce non-specific or premature PCR amplification.

Aside from hot start region 3258 and its associated gap and core portion, the remainder of thermocycler 3200, which is generally indicated at 3262, may have a similar construction to thermocycler 3200 described previously. Alternatively, instead of thermoelectric coolers, thermocycler 3200 may include an air core surrounded by a plurality of resistive section heaters (not shown) for heating various temperature regions 3263, 3265, 3267 of the thermocycler. These regions may be separated by insulating gaps 3269, 3271, which extend into an insulating base portion 3273 to help thermally isolate the temperature regions from each other. The configuration of the base portion, including the insulating gaps, can be changed to adjust thermal conductance between the different temperature regions.

Example 2

Exemplary Heating Configurations for Thermocyclers

This example describes various exemplary heating configurations for exemplary thermocyclers 3202*a-h* in accordance with aspects of the present disclosure; see FIGS. 11-18.

FIGS. 11-18 are schematic diagrams depicting top views of the thermocyclers. These diagrams, like FIG. 7, correspond to and are topologically equivalent to three-dimensional cylindrical thermocycling units. The thermocyclers each include three inner (e.g., melt, anneal, and extend) segments 3204*a-h*, 3206*a-h* 3208*a-h* in thermal contact with fluidic tubing 3218*a-h* for carrying samples undergoing PCR. The segments, in turn, each may (or optionally may not) be in thermal contact with respective (e.g., melt, anneal, and extend) heating elements 3254*a-h*, 3256*a-h*, 3258*a-h* (denoted by vertical bars) for delivering heat to the segments. The segments also may be in direct or indirect contact with one or more TECs (indicated by cross-hatching), one or more thermal conductive layer(s) (indicated by stippling), one or more thermal insulating layer(s) (indicated by dashed-dotted hatching), and/or one or more heated or unheated cores (indicated by hatching or stippling, respectively). These and other components of the thermocyclers may be selected and initially and/or dynamically adjusted to establish, maintain, and/or change the absolute and relative temperatures of the different segments and thus of the associated fluidic tubing and PCR samples. Specifically, the components may be selected and/or adjusted to accomplish a temperature goal by accounting for heat added to or removed from the segments via conduction through other components (including fluidic tubing and the associated fluid) and/or convection with the environment. In particular, the TECs, where present, may transfer heat to or from the segments to facilitate more rapid and precise control over the associated segment temperatures and thus the associated reaction temperatures.

Figure 11:
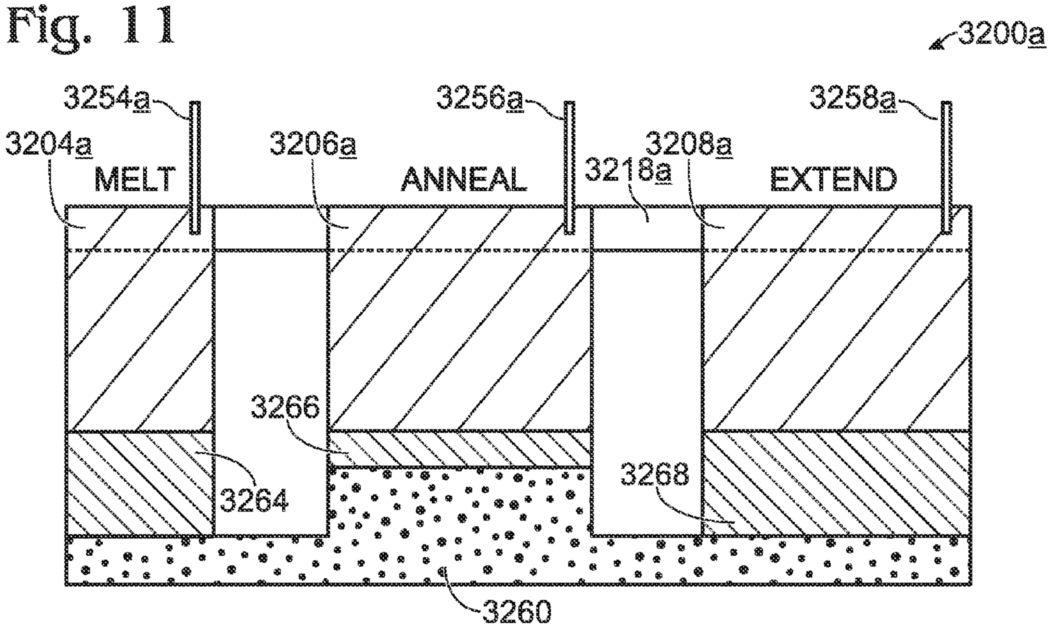
FIGS. 11-18 are schematic sectional views of alternative embodiments of a thermocycler, in accordance with aspects of the present disclosure.

FIG. 11 depicts a first alternative thermocycler 3200*a*. In this embodiment, the melt, anneal, and extend segments 3204*a*, 3206*a*, and 3208*a* are in thermal contact with a common unheated (e.g., plastic block) core 3260 via respective thermal insulating layers 3264, 3266, 3268. The insulating layers (and insulating layers described elsewhere in this section) independently may be made of the same or different materials, with the same or different dimensions, such that the layers may have the same or different thermal conductivities. For example, in this embodiment, the insulating layers for the melt and extend segments are made of the same material, with the same thickness, whereas the insulating layer for the anneal segment is made of a different material, with a different thickness. Heat for performing PCR is supplied to the segments by heating elements 3254*a*, 3256*a*, 3258*a*. This embodiment is particularly simple to construct, with relatively few, mostly passive components. However, it is not as flexible or responsive as the other pictured embodiments.

Figure 12:
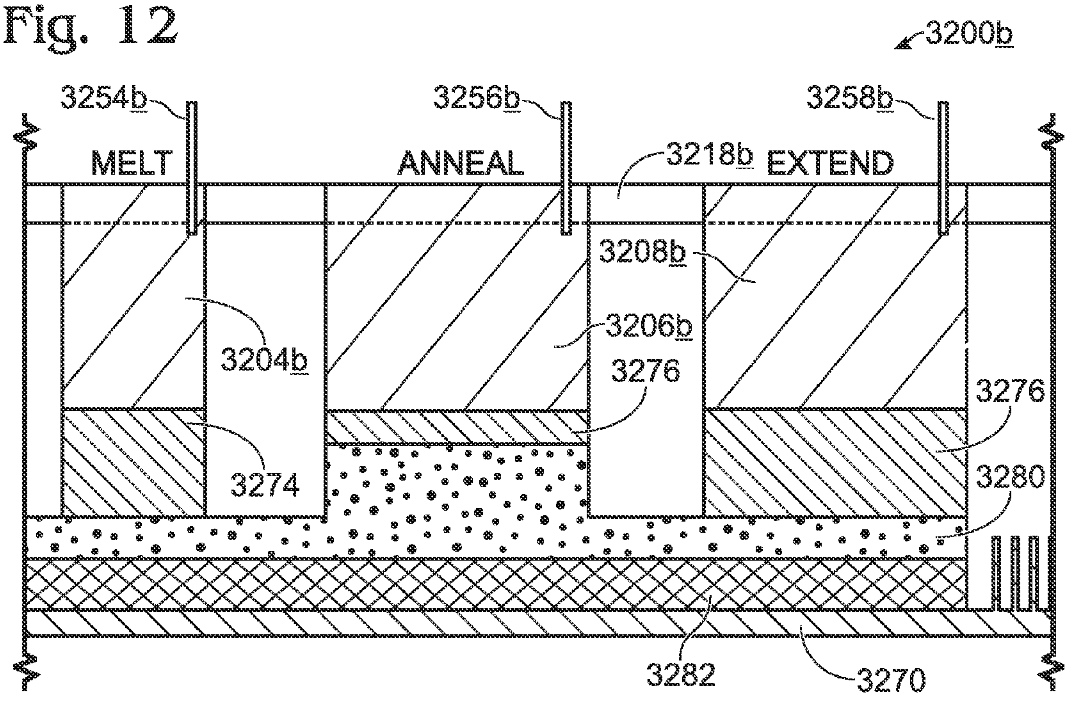

FIG. 12 depicts a second alternative thermocycler 3200*b*. In this embodiment, the melt, anneal, and extend segments 3204*b*, 3206*b* and 3208*b* are in thermal contact with a common heated (e.g., copper) core 3270. However, disposed between the segments and the core, preventing their direct contact, are respective insulating layers 3274, 3276, 3278 (one for each segment), a common thermal conductor 3280 (in contact with all three insulating layers), and a common TEC 3282 (in contact with the common thermal conductor and with the common heated core). Heat for performing PCR is supplied to the segments by heating elements 3254*b*, 3256*b*, 3258*b* and by the common core. The TEC may be used to transfer heat to and from the inner segments and the heated core, across the intervening insulating and conducting layers, to adjust, up or down, the temperatures of the segments.

Figure 13:
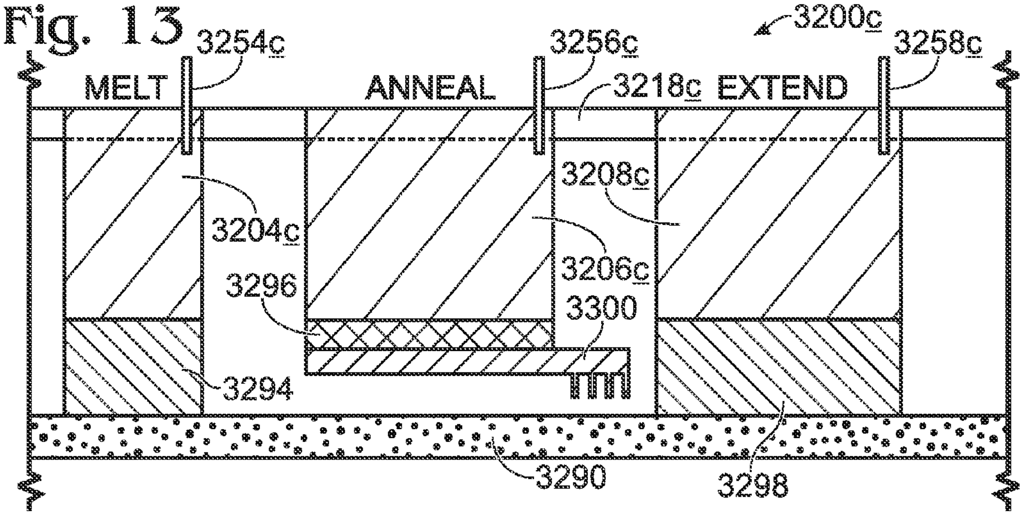

FIG. 13 depicts a third alternative thermocycler 3200*c*. In this embodiment, the melt and extend segments 3204*c* and 3208*c* are in thermal contact with a common unheated core 3290 via respective insulating layers 3294, 3298, whereas the anneal segment 3206*c* is in thermal contact with a heated core 3300 via a dedicated intervening TEC 3296. This configuration substantially thermally decouples the anneal segment from the melt and extend segments and allows the temperature of the anneal segment to be changed relatively rapidly via heating element 3256*c*, heated core 3300, and the TEC. The temperatures of the melt and extend segments, which are thermally connected through unheated core 3290, may be changed via heating elements 3254*c*, 3258*c* (to add heat) and conduction to the unheated core (to remove heat).

Figure 14:
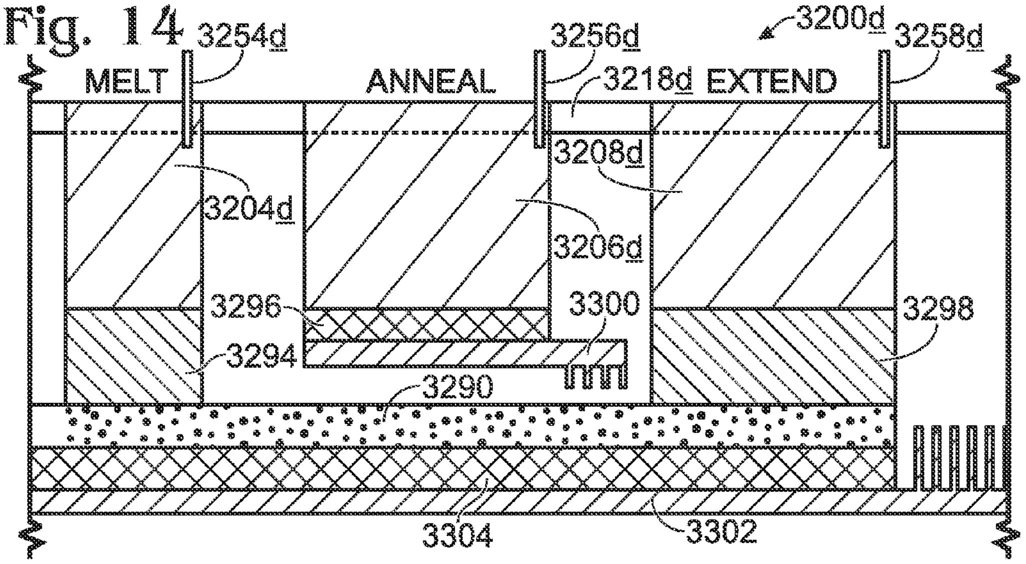

FIG. 14 depicts a fourth alternative thermocycler 3200*d*. In this embodiment, thermocycler 3200*c* (from FIG. 13) is further coupled to a common heated core 3302 via an intervening TEC 3304, allowing enhanced feedback and control over the temperatures of the melt and extend segments via the TEC layer.

Figure 15:
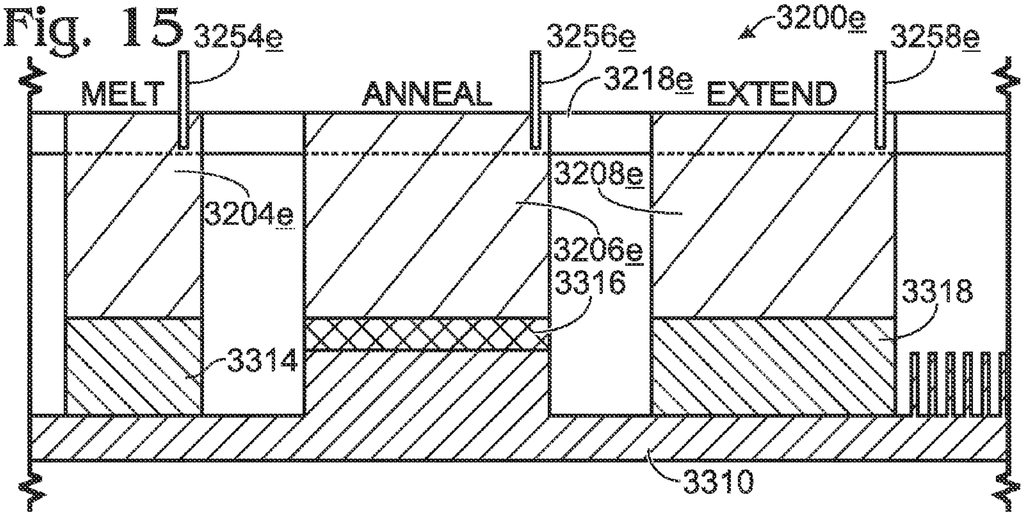

FIG. 15 depicts a fifth alternative thermocycler 3200*e*. In this embodiment, the melt, anneal, and extend segments 3204*e*, 3206*e*, 3208*e* are in thermal contact with a common heated core 3310 via either a dedicated insulating layer 3314, 3318 (in the case of the melt and extend segments) or a dedicated TEC layer 3316 (in the case of the anneal layer). This configuration allows relatively rapid feedback and control over the temperature of the anneal segment via a combination of the heating element 3256*e* and the TEC, while still providing a measure of control over the temperatures of the melt and extend segments via heating elements 3254*e*, 3258*e*.

Figure 16:
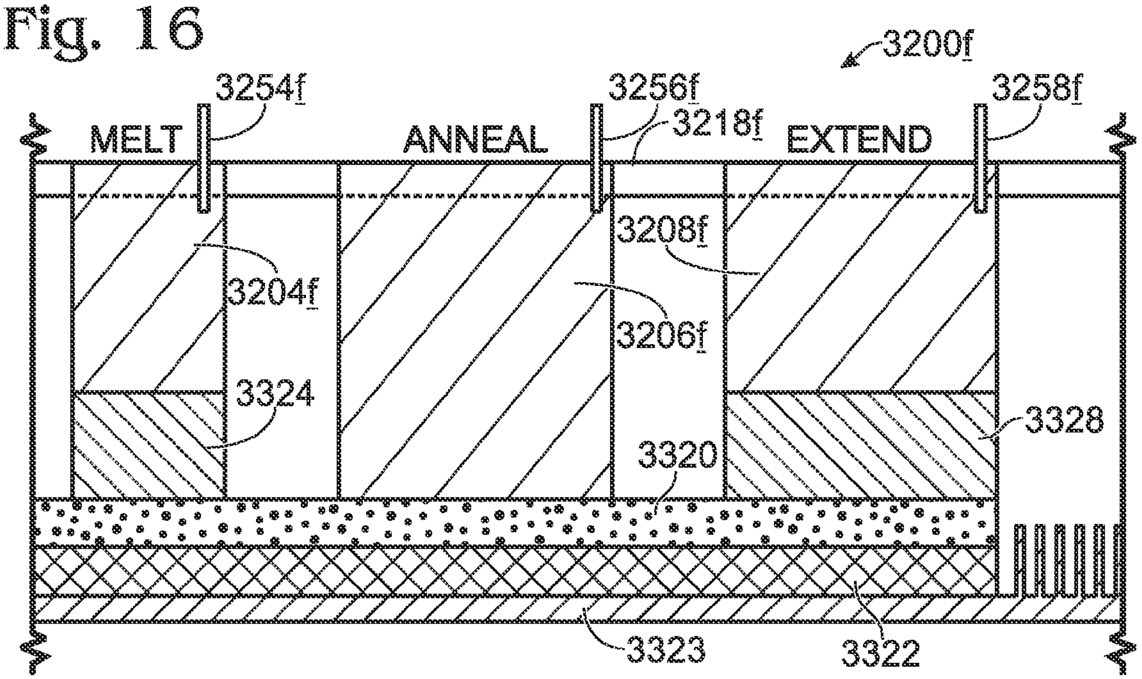

FIG. 16 depicts a sixth alternative thermocycler 3200*f*. In this embodiment, which is similar to thermocycler 3200*e* of FIG. 15, a common conducting layer 3320 and a common TEC 3322 separate the segments from the entirety of a heated thermal core 3323. The TEC is in thermal contact with the anneal segment through the conducting layer, whereas the TEC is separated from the melt and extend segments both by the conducting layer and by dedicated insulating layers 3324, 3328.

Figure 17:
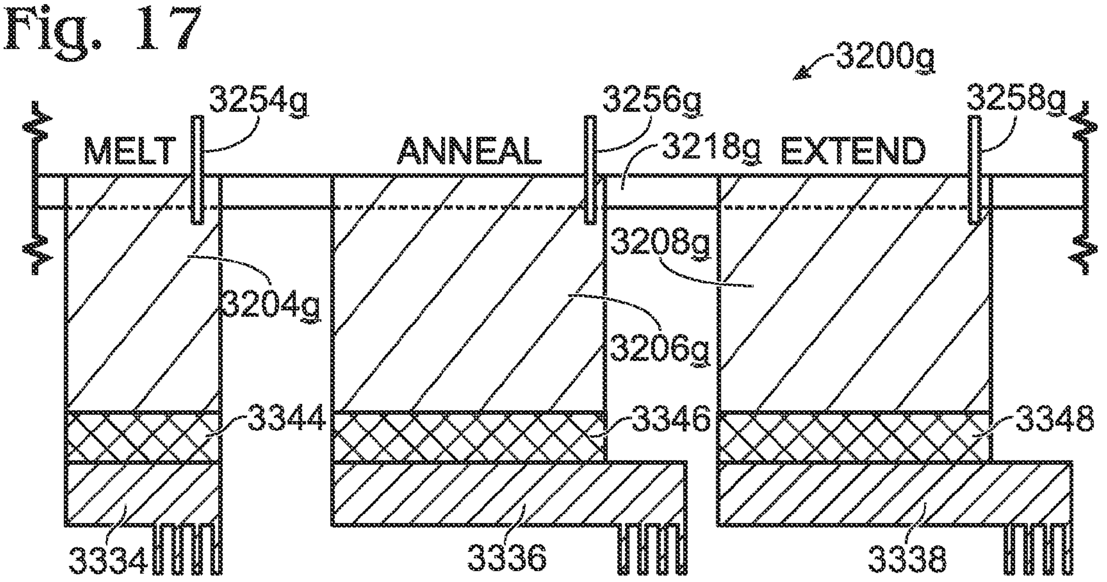

FIG. 17 depicts a seventh alternative thermocycler 3200*g*. In this embodiment, the melt, anneal, and extend segments 3204*g*, 3206*g*, 3208*g* each are in thermal contact with a respective heated core 3334, 3336, 3338 via a dedicated intervening TEC 3344, 3346, 3348 (for a total of three segments, three heated cores, and three TECs). This embodiment provides rapid feedback and separate control over the temperature of each inner segment. In particular, each segment is independently in thermal contact with dedicated heating element and a dedicated heated core, such that heat can be transferred to or from the segment from two dedicated sources or sinks. However, this embodiment also is more complicated, requiring controllers for each TEC.

Figure 18:
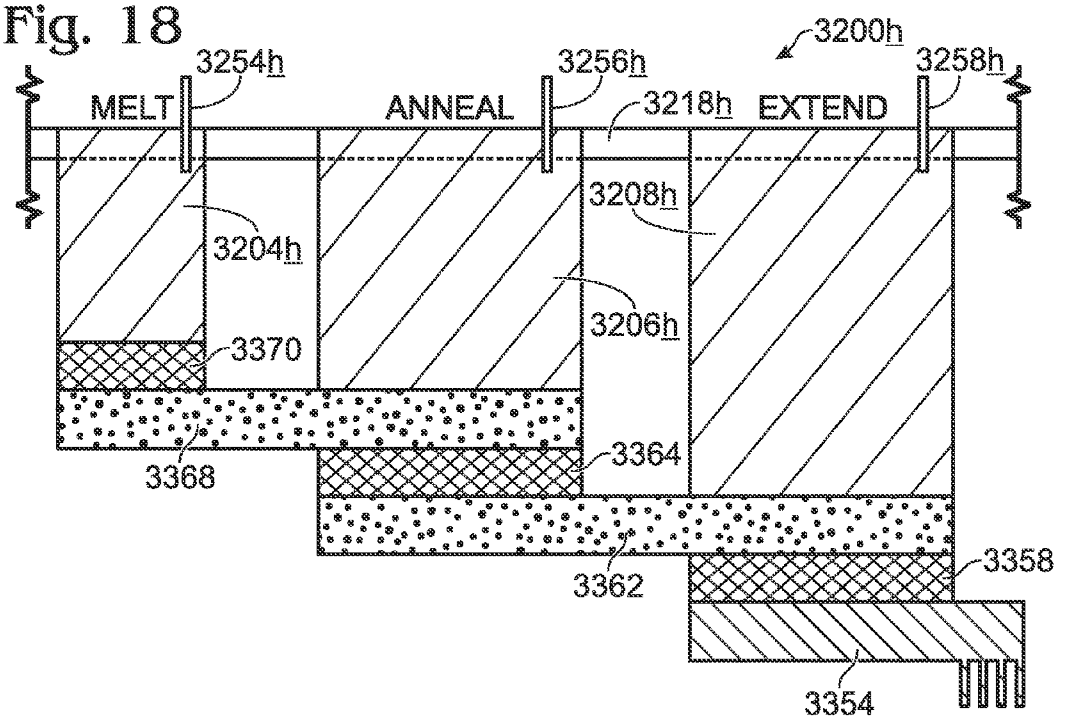

FIG. 18 depicts an eighth alternative thermocycler 3200*h*. In this embodiment, in which a single section of a heated core 3354 is aligned interior to one inner segment (e.g., the extend segment 3208*h*) of the thermocycler, separated from the segment by a TEC 3358. The extend segment, in turn, is in thermal contact with a neighboring inner segment (e.g., the anneal segment 3206*h*) via an unheated conductor 3362, which is separated from the inner segment by a second TEC 3364. The anneal segment, in turn, is in thermal contact with a neighboring inner segment (e.g., melt segment 3204*h*) via another unheated conductor 3368, which is separated from the inner segment by a third TEC 3370. Thus, core section 3354 remains available to all of the TECs as a heat source and heat sink.

Example 3

Exemplary Thermocycler Instrument

Figure 19:
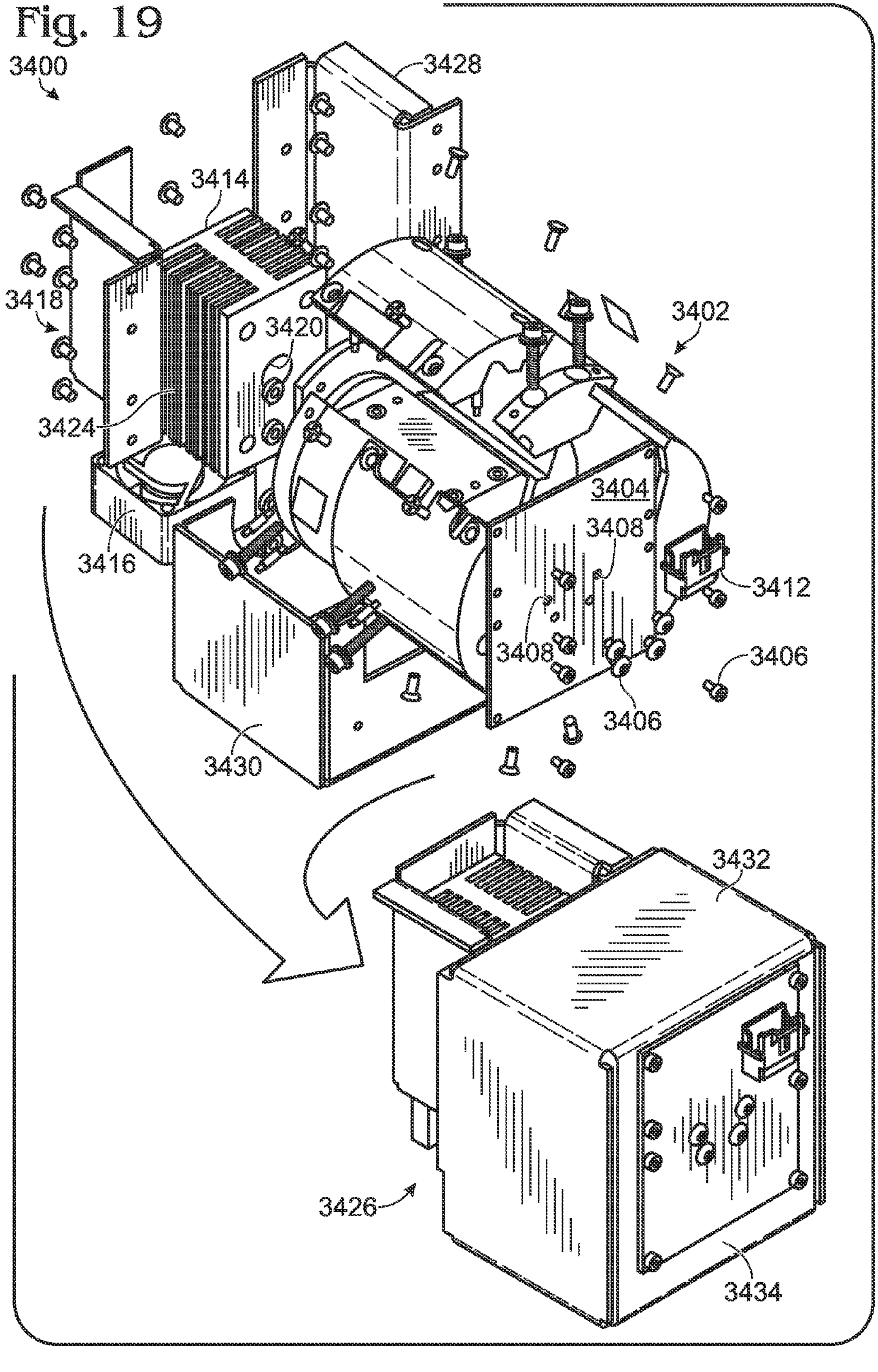
FIG. 19 is an exploded isometric view of a thermocycler, with associated heating, cooling, and housing elements, in accordance with aspects of the present disclosure.

This example describes a thermocycler disposed within an exemplary instrument that also includes other components such as a cooling mechanism and a protective housing; see FIG. 19.

FIG. 19 generally depicts an exemplary thermocycling instrument 3400 at various stages of assembly. Instrument 3400 includes a thermocycler, generally indicated at 3402, which is substantially similar to thermocycler 3200 described above, but which generally may take various forms, including one or more features of any of the thermocyclers described in the previous examples. The instrument may include additional components, such as a front plate, a connection port, a heat sink, a cooling fan, and/or a housing, as described below.

A front plate 3404 is attached to the thermocycler with a plurality of fasteners 3406 that pass through central apertures 3408 in the front plate and complementary apertures in the thermocycler. The front plate helps to isolate the thermocycler from external air currents and thus to maintain controlled temperature zones within the unit.

A connection port 3412 is attached to the front plate, and is configured to supply power to the instrument and to receive sensor information obtained by the instrument. Thus, the connection port is configured to receive electrical power from outside the instrument and transmit the power to the instrument, and to receive sensor signals from within the instrument and transmit the signals outside the instrument. Transfer of power and sensor signals may be accomplished through suitable connecting wires or cables (not shown) disposed within and outside the instrument.

A heat sink 3414 and a cooling fan 3416, which will be collectively referred to as a cooling mechanism 3418, are shown attached to a side of the thermocycler opposite the front plate. One or both components of cooling mechanism 3418 will generally be mounted to the thermocycler using suitable fasteners such as bolts, pins and/or screws. In FIG. 19, heat sink 3414 is attached directly to the thermocycler, and cooling fan 3416 is attached to the heat sink. Heat sink 3414 includes a central aperture 3420, which is aligned with a central aperture of the thermocycler (see, e.g., FIGS. 2, 3 and 6). These aligned apertures facilitate heat transfer from the central (axial) portion of thermocycler 3402 into the heat sink. The heat sink also may be formed of a relatively thermally conductive material to facilitate conduction of excess heat away from the thermocycler, and includes convection fins 3424 to facilitate convection of heat away from the thermocycler.

Cooling fan 3416 is configured to blow cooling air through fins 3424 and aperture 3420 of the heat sink, to increase convective heat transfer away from the heat sink. Air from fan 3416 also may flow or be directed through the heat sink and into the central aperture of thermocycler 3402, to provide a convection current within the thermocycler. Dedicated structures such as baffles, angled walls, or canted fins (not shown) may be provided to facilitate the transfer of air from the cooling fan into the thermocycler.

Thermocycler 3402 and cooling mechanism 3418 are mounted within an external housing, generally indicated at 3426. Housing 3426 may include several discrete sections 3428, 3430, 3432, 3434, which are configured to conform to various portions of the thermocycler and the cooling mechanism, and which are further configured to fit together and interface with front plate 3404 to form housing 3426. The various discrete sections and the front plate of housing 3426 are collectively configured to insulate the thermocycler from external air currents and other factors that could lead to uncontrolled temperature variations within the thermocycler.

Example 4

Temperature Regions Varying in Size and/or Number

Figure 20:
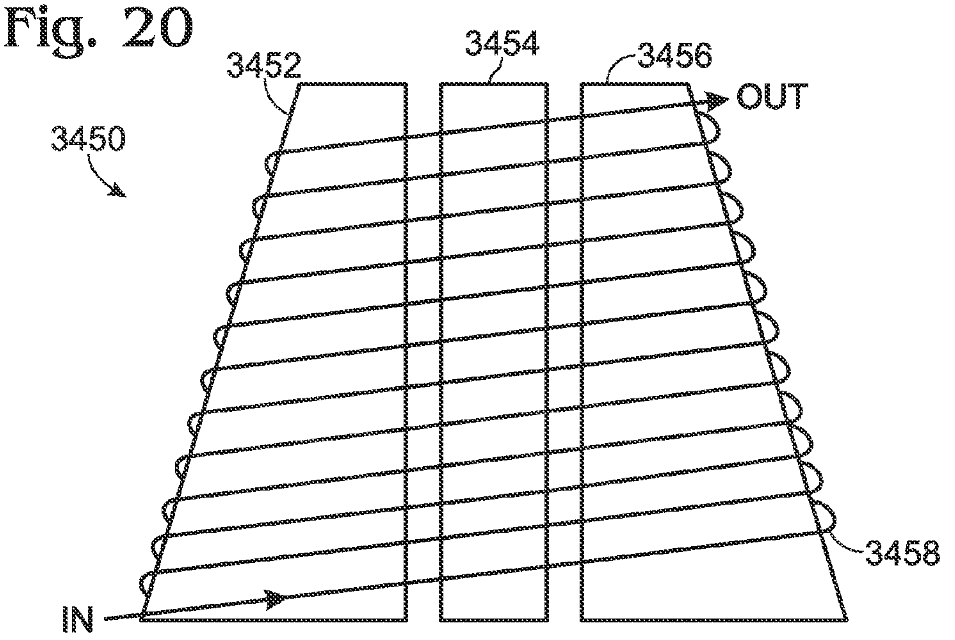
FIG. 20 is a side elevational view of an exemplary thermocycler having temperature regions that vary in size along the length of the thermocycler, in accordance with aspects of the present disclosure.
Figure 21:
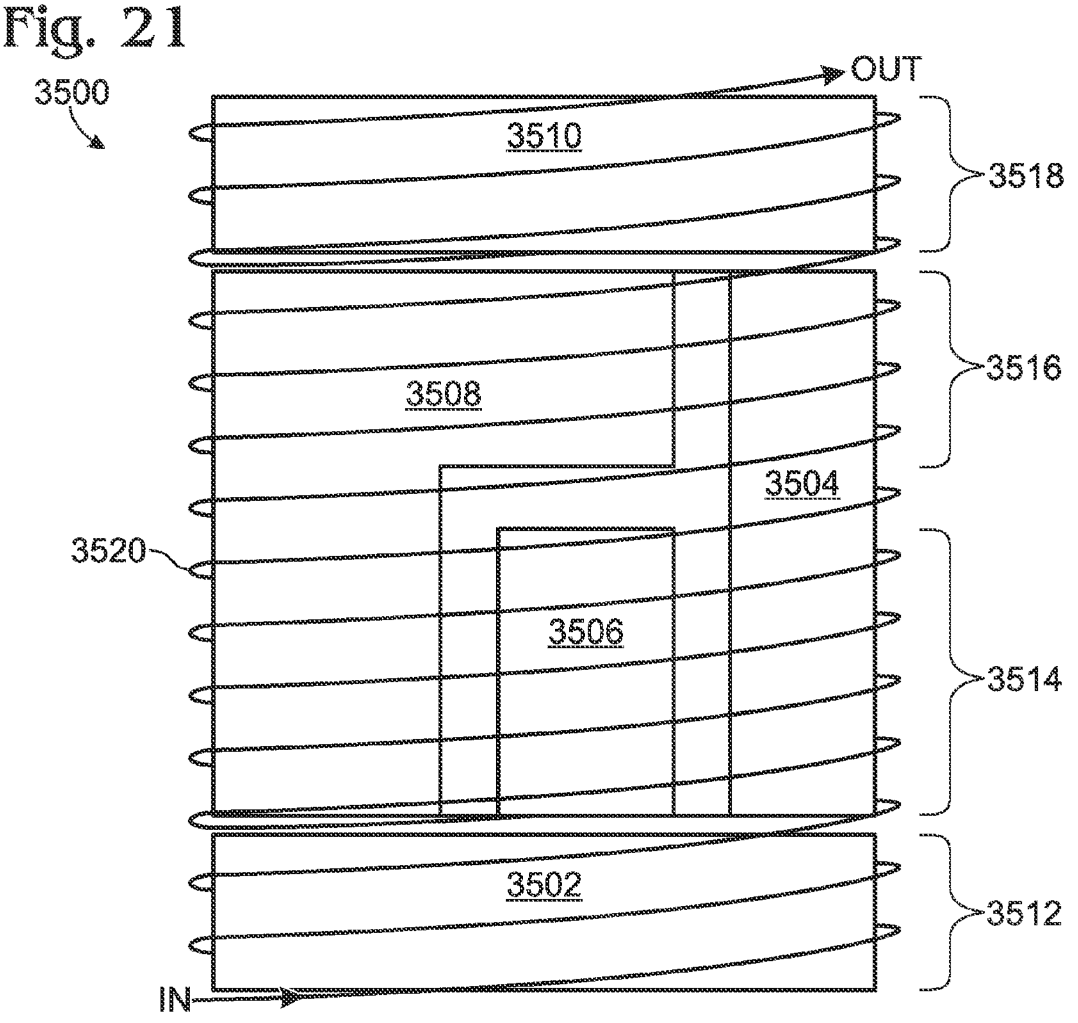
FIG. 21 is a side elevational view of an exemplary thermocycler having temperature regions that vary in number along the length of the thermocycler, in accordance with aspects of the present disclosure.

This example describes exemplary thermocyclers having temperature regions that vary in size and/or number along the length of the thermocycler, in accordance with aspects of the present disclosure; see FIGS. 20 and 21.

FIG. 20 shows a side elevational view of portions of an exemplary thermocycler, generally indicated at 3450, having three connected segments 3452, 3454, 3456, each defining a different temperature region. Segments 3452, 3454, 3456 may be connected via a common core or through materials (typically thermally insulating materials), not shown, disposed between the segments. Segments 3452, 3454, 3456 are angled along the length of the thermocycler (i.e., along the longitudinal axis), so that the inner segments of thermocycler 3450 collectively form a generally frustoconical shape as FIG. 20 depicts. Accordingly, each winding of fluidic tubing 3458 wrapped around the exterior of thermocycler 3450 will be progressively shorter from bottom to top in FIG. 20, so that the helical path followed by the tubing decreases in length over successive cycles. Assuming fluid flows through tubing 3458 at a uniform speed, fluid within the tubing will therefore spend progressively less time in the temperature regions defined by segments 3452 and 3456. On the other hand, segment 3454 has a substantially constant width, so that fluid flowing through tubing 3458 will spend a substantially constant amount of time in the corresponding temperature region with each successive cycle, again assuming the fluid flows with a uniform speed.

The thermocycler depicted in FIG. 20 may be useful, for example, when it is desirable to begin a thermocycling operation with cycles of relatively long duration, and subsequently to decrease the cycle duration to speed up the overall thermocycling process. In applications such as PCR, decreasing the cycle duration may be expedient because efficient target molecule replication becomes increasingly less important with each successive thermocycle. For instance, if a single target molecule fails to replicate during the first cycle and then replicates with perfect efficiency in the subsequent 19 cycles, the result after 20 cycles will be $2^{19}$ target molecules. However, if a single target molecule replicates with perfect efficiency for the first 19 cycles, but one molecule fails to replicate during the twentieth cycle, the result after 20 cycles will be $(2^{20}-1)$ target molecules.

Aside from a frustoconical shape, many other thermocycler configurations can be used to affect the time of passage of a sample fluid through the various temperature regions of a thermocycler. For example, the sizes of various temperature regions may be decreased in discrete steps, by sequentially decreasing the radius of a cylindrical thermocycler in discrete steps. In general, any configuration that results in a changing path length traveled by successive windings of fluidic tubing may be suitable for altering the time a fluid spends at each desired temperature over the course of the entire thermocycling process.

FIG. 21 shows a side elevational view of portions of an exemplary thermocycler, generally indicated at 3500, having temperature regions that vary in number along the length of the thermocycler, in accordance with aspects of the present disclosure. Specifically, thermocycler 3500 includes a plurality of inner segments 3502, 3504, 3506, 3508, 3510 that each may be configured to define a separate temperature region. These segments may be attached to a common core (not shown) or bound together in any suitable manner, and may be separated by air or any other suitable medium, typically a thermally insulating material. The gaps, if any, between segments may have any chosen widths to generate a desired temperature profile in both the longitudinal direction and the tangential direction. As FIG. 21 depicts, the plurality of inner segments includes a different number of inner segments attached to the core at different positions along the longitudinal axis.

Fluid traveling through fluidic tubing 3520 would encounter a first portion 3512 of the thermocycler having just a single temperature region defined by segment 3502. Subsequently, the fluid would encounter a second portion 3514 of the thermocycler having three temperature regions defined by segments 3504, 3506, and 3508. Next, the fluid would encounter a third portion 3516 of the thermocycler having two temperature regions defined by segments 3504, 3508, and finally the fluid would encounter a fourth portion 3518 of the thermocycler having a single temperature region defined by section 3510.

In some embodiments, the number of temperature regions may vary along the central axis to produce more than one complete thermal cycle per revolution of the fluid channel about the central axis. In particular, temperature regions may be duplicated at some positions, and not others, along the central axis. For example, closer to the inlet of the fluid channel, the fluid channel may extend through only one complete thermal cycle (e.g., denature, anneal, and extend) per revolution about the central axis and then, closer to the outlet of the fluid channel, may extend through two or more complete thermal cycles (e.g., denature, anneal, and extend, followed by another round of denature, anneal, and extend). Thus, the cycle duration may be relatively longer closer to the inlet and then relatively shorter closer to the outlet.

Any desired number of longitudinal portions, instead of or in addition to portions 3512, 3514, 3516 and 3518, may be included in a thermocycler, to alter the number of temperature regions encountered by a fluid as it proceeds through a thermocycling process. Furthermore, any desired number of tangential segments may be included within each longitudinal portion, so that particular windings of fluidic tubing may be configured to encounter essentially any number of temperature regions. By combining the features of thermocycler 3500 with the features of thermocycler 3450 depicted in FIG. 20, a thermocycler can be constructed to provide virtually any temporal temperature profile to a moving fluid, making the disclosed thermocyclers suitable for a wide range of applications.

Example 5

Thermocycler Aspects and Variations

This example describes various additional aspects and possible variations of a thermocycler, in accordance with aspects of the present disclosure.

Whereas thermocyclers are primarily described above as including a single "strand" of fluidic tubing wrapped substantially helically around the circumference of heated sections of the thermocycler, many variations are possible. For example, more than one strand of tubing may be provided, and the various strands all may be wrapped around a portion of the thermocycler. In some cases, the strands may be braided in some fashion so that they cross each other repeatedly, whereas in other cases the strands all may be configured to directly contact the heated thermocycler sections for substantially the entirety of their wrapped length. In addition, one or more tubes may be configured to pass through the heated sections of a thermocycler, rather than wrapped around their exteriors. For instance, the heated sections may be cast, molded, or otherwise formed around the tubes. In some cases, fluid tight channels may be formed in this manner, so that tubes are not necessary.

In some cases it may be desirable to vary the number of thermocycles provided by a thermocycling instrument, either dynamically or by providing several varying options for the number of cycles a particular fluid will encounter. Dynamic changes in the number of thermocycles may be provided, for example, by unwinding or additionally winding the fluidic tubing around the thermocycler. Optional numbers of cycles may be provided, for example, by providing multiple fluidic tubes that are wound a different number of times around the instrument, or by creating various optional bypass mechanisms (such as bypass tubes with valves) to selectively add or remove cycles for a particular fluid.

Although the heated segments of the thermocyclers described above are generally shown separated from each other by thermally insulating air gaps, any desired thermally insulating material may be placed between the heated segments of a thermocycler according to the present disclosure. For example, the use of a low-density polymer or a silica aerogel may provide increased thermal isolation of neighboring segments, both by reducing the thermal conductivity of the insulating regions and by decreasing convective heat transfer.

The fluid channel(s) of the thermocycler may carry any suitable fluid. The fluid may comprise an aqueous phase and a non-aqueous phase(s). The non-aqueous phase(s) may be or include a continuous phase (and/or a carrier phase), and may or may not include a barrier phase. The aqueous phase may be a dispersed phase, which may be composed of discrete droplets. The behavior of a single-phase fluid should be different from that of a two-phase fluid. In the single-phase case, portions of the fluid near the walls of the fluid channel travel more slowly (longer cycle times), while portions of the fluid near the center of the channel travel more quickly (shorter cycle times). Thus, single-phase fluid that exits the fluid channel will have been exposed to a mixture of short and long cycle times. In contrast, droplets at a relatively low packing density in the fluid channel may tend to flow in the center of the channel to produce more uniform cycle times, and/or a barrier phase may be used to trap (i.e., push and/or retard) the droplets at a relatively high (or medium or low) packing density in the fluid channel so the droplets produce a more uniform cycle time. Further aspects of the use of a barrier phase and various droplet packing densities in the fluid channel are described below in Example 6.

The disclosed thermocyclers may be used for PCR, any other molecular amplification process, or indeed any process involving cyclical temperature changes of a fluid sample, whether or not the sample includes discrete droplets. For example, potentially target-containing samples may be separated into discrete units other than droplets, such as by binding sample molecules to a carrier such as a suitable bead or pellet. These alternative carriers may be placed in a background fluid and thermocycled in much the same way as droplets in an emulsion. Alternatively, a plurality of thermocyclers may be used simultaneously to cycle different bulk fluid samples in parallel or in an overlapping sequence, without separating the fluid samples into many discrete units.

Example 6

Exemplary Thermocycling System

This example describes an exemplary thermocycling system 3550; see FIGS. 22-28. The system may be used to thermally cycle sample droplets disposed in a carrier fluid. The droplets optionally may be bounded upstream and/or downstream by a barrier fluid that limits dispersion of the droplets along the thermocycler channel and/or that maintains separation of different sets of droplets from one another, among others.

Figure 22:
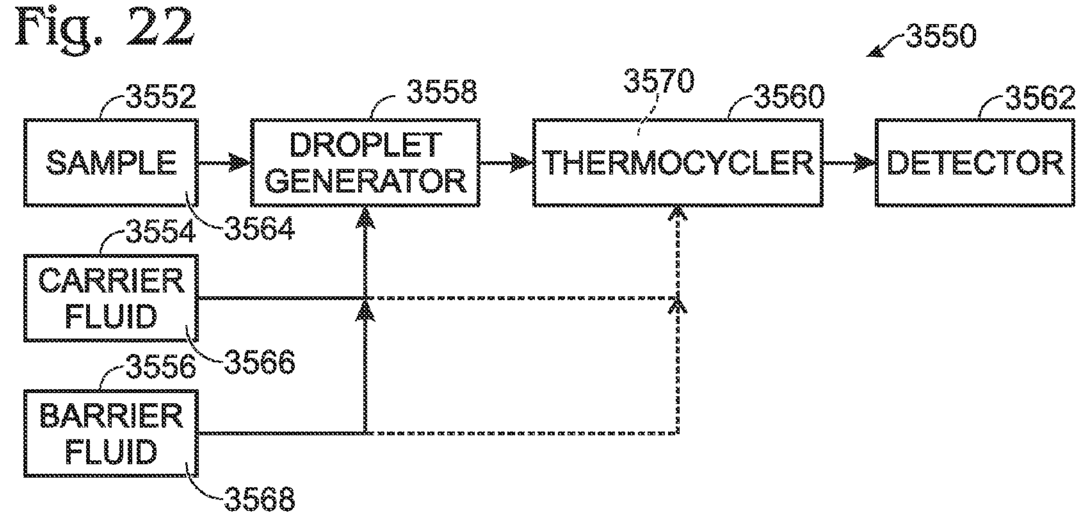
FIG. 22 is a schematic view of an exemplary thermocycling system including a droplet generator, a thermocycler, and a detector, in accordance with aspects of the present disclosure.

FIG. 22 depicts exemplary components of thermocycling system 3550 including fluid reservoirs 3552-3556, which may supply fluid to any combination of at least one droplet generator 3558, a thermocycler 3560, and a detector 3562, among others. The reservoirs may include a sample reservoir 3552 containing a sample 3564, a carrier reservoir 3554 containing a carrier fluid 3566 (e.g., oil), and a separator reservoir 3556 containing a barrier fluid 3568 (e.g., another oil, an aqueous fluid, or a gas (such as air, nitrogen, an inert gas, etc.), among others). The sample, carrier fluid, and barrier fluid, may form discrete phases, namely, a droplet or dispersed phase, a continuous or carrier phase, and a barrier or separator phase, respectively.

"Oil" may be any liquid (or liquefiable) compound or mixture of liquid compounds that is immiscible with water. The oil may be synthetic or naturally occurring. The oil may or may not include carbon and/or silicon, and may or may not include hydrogen and/or fluorine. The oil may be lipophilic or lipophobic. In other words, the oil may be generally miscible or immiscible with organic solvents. Exemplary oils may include at least one silicone oil, mineral oil, fluorocarbon oil, vegetable oil, or a combination thereof, among others. In some embodiments, the carrier fluid and the barrier fluid may be composed of respective fluids, such as distinct oil compositions or oil and a gas, that are immiscible with each other.

Exemplary directional movement of fluid within system 3550, such as by flow and/or via a fluid transfer device (e.g., a pipette), is indicated by arrows. Accordingly, the arrows of FIG. 22 may represent channels, which may form inlets, outlets, and/or injection orifices, among others, to introduce fluid to and/or remove fluid from, the droplet generator(s), thermocycler, and/or detector. The carrier fluid and/or barrier fluid may be introduced into a fluid channel 3570 of thermocycler 3560 via a droplet generator(s) and/or at a position(s) downstream of the droplet generator(s), as indicated by dashed arrows that extend to the thermocycler in FIG. 22.

In some embodiments, one or more isolated volumes or partitions of barrier fluid 3568 may be formed (e.g., by an injector, operation of a valve, a droplet generator, or a combination thereof, among others) for introduction into fluid channel 3570. In any event, as described further below, each partition of the barrier fluid may be large enough to limit droplet movement along channel 3570, past the partition, which creates a moving barrier to droplet dispersion.

Droplets may be formed by droplet generator(s) 3558 using sample 3564 and, optionally, carrier fluid 3566. The droplet generator may be connected or connectable to the thermocycler, to provide transfer of the droplets to fluid channel 3570. Further aspects of droplet generators that may be suitable are disclosed in the documents listed above under Cross-References, which are incorporated herein by reference, particularly, U.S. patent application Ser. No. 12/586,626, filed Sep. 23, 2009.

Droplets may be transported through fluid channel 3570 of thermocycler 3560 to heat and cool the droplets cyclically. The thermocycler may have any combination of the features disclosed herein and/or in the documents listed above under Cross-References, which are incorporated herein by reference, particularly, U.S. patent application Ser. No. 12/586,626, filed Sep. 23, 2009.

Data may be collected from the thermally cycled droplets using detector 3562. The detector may have any combination of the features disclosed herein and/or in the documents listed above under Cross-References, which are incorporated herein by reference, particularly, U.S. patent application Ser. No. 12/586,626, filed Sep. 23, 2009.

Figure 23:
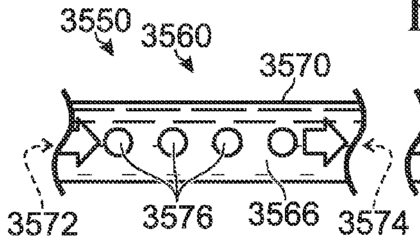
FIG. 23 is a fragmentary view of a fluid channel of the thermocycler of FIG. 22, with a relatively low density of droplets being transported in single file along the fluid channel in a carrier fluid, with the droplets traveling in a low-density flow regime, in accordance with aspects of present disclosure.

FIG. 23 shows a fragmentary view of fluid channel 3570, taken between an inlet 3572 and an outlet 3574 of the channel. (The direction of fluid flow in FIGS. 23-27 is indicated by open arrows.) The fluid channel may contain droplets 3576 formed by droplet generator 3558 (see FIG. 22), and also may contain carrier fluid 3566 in which the droplets are disposed. Channel 3570 may follow any suitable path (e.g., a helical path, a planar path, or the like) to provide thermal cycling of fluid traveling through the channel.

The inner diameter of fluid channel 3570 relative to the diameter of droplets 3576 may form any suitable ratio. For example, the ratio may be less than about five, greater than about five, or between about one and five, among others. As a more specific example, for illustration only, channel 3570 may have an inner diameter of 250 to 500 microns, and droplets 3576 may have a diameter of 100 to 150 microns.

FIG. 23 depicts a relatively low packing density of droplets 3576 being transported in single file along the center of fluid channel 3570. The droplets tend to be centered at this lower density because, due to the parabolic profile of flow velocity produced by laminar flow in the channel, fluid flows fastest at the channel center and slowest near the channel wall. In this low-density regime, droplets tend to travel at about the same velocity, thereby minimizing variations in thermal cycling times among the droplets. However, in some cases, where fluid velocity is inadequate, and the fluid density difference between the droplets and the carrier fluid is substantial, gravity may affect droplet position by causing the droplets to move off-center through buoyancy effects. For example, carrier fluid may slip underneath droplets that float toward or against the upper wall of the fluid channel, causing these buoyed droplets to move more slowly than the carrier fluid and/or than more centrally situated droplets (which may produce differential rates of travel of droplets).

Figure 24:
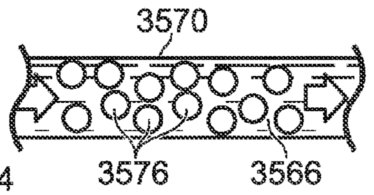
FIG. 24 is a view of the fluid channel of FIG. 23, with an intermediate density of droplets being transported along the fluid channel in a medium-density flow regime in which droplets may travel at different rates along the channel, in accordance with aspects of present disclosure.

FIG. 24 depicts an intermediate (medium) packing density of droplets 3576 being transported along fluid channel 3570. Here, the packing density of droplets in the channel is much higher than in FIG. 23. As a result, in this medium-density flow regime, the droplets cannot all fit in the center of the channel and thus droplets tend to travel at different velocities through the thermocycler, thereby increasing variation in thermal cycling times among the droplets.

Figure 25:
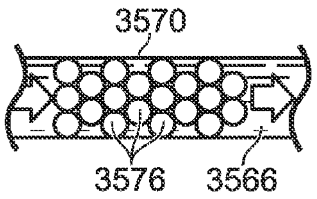
FIG. 25 is a view of the fluid channel of FIG. 23, with a relatively high density of droplets being transported along the fluid channel in a high-density flow regime in which the droplets are packed closely together along and across the fluid channel, to form a crystal-like lattice that moves along the fluid channel as a unit, in accordance with aspects of present disclosure.

FIG. 25 depicts a relatively high packing density of droplets 3576 being transported along fluid channel 3570. As a result, in this high-density flow regime, the droplets are packed closely together along and across the fluid channel, to form a crystal-like lattice that moves along the fluid channel as a unit.

A single-file and/or low-density flow regime allows the droplets to be generally centered in the fluid channel. Droplet centering may be permitted by a ratio of the droplet phase to the carrier phase that is sufficiently low. In other words, all of the droplets fit in a central region of the channel without forcing a substantial number of the droplets to lateral positions in the channel. Alternatively, or in addition, a single-file flow regime may be produced by a fluid channel that is sufficiently narrow relative to the droplet diameter to restrict droplets from passing one other in the fluid channel, independent of their density. For example, the inner diameter of the fluid channel may be less than about twice the diameter of the droplets. Droplets in a single-file or low-density flow regime generally travel at about the same rate through the fluid channel, thereby producing a uniform thermal cycle time for the droplets.

A medium-density flow regime has a sufficient packing density of droplets to prevent all of the droplets from fitting centrally in the fluid channel, without packing the droplets so closely that they travel as a unit. In this regime, due to laminar flow, droplets closer to the channel wall may form an outer shell and more centered droplets may occupy an inner core that "slips" past the outer shell. With this intermediate density, the thermal cycle time generally is not uniform because droplets in the outer shell experience longer thermal cycle times than those in the inner core.

A high-density flow regime has a sufficiently high packing density of droplets to cause droplets to move together as a unit through the fluid channel. In a high-density flow regime, the droplets may be packed close enough to one another to form a crystal-like lattice. As a result, the lattice slips along the channel as a unit. Thus, a high-density flow regime may overcome differential travel rates of droplets caused by laminar flow in medium-density flow regimes and/or by droplet buoyancy effects.

Figure 26:
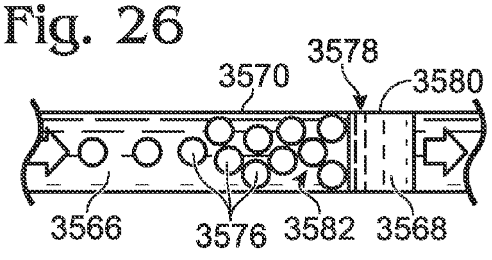
FIG. 26 is a view of the fluid channel of FIG. 23, with a barrier fluid disposed downstream of a packet of droplets, in accordance with aspects of the present disclosure.
Figure 27:
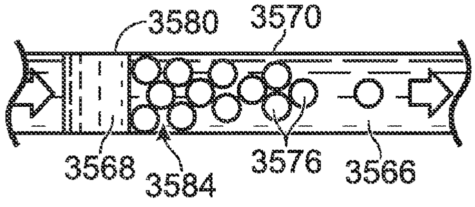
FIG. 27 is a view of the fluid channel of FIG. 23, with a barrier fluid disposed upstream of a packet of droplets, in accordance with aspects of the present disclosure.
Figure 28:
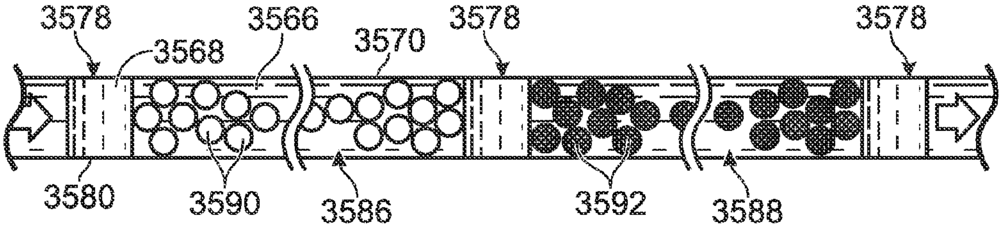
FIG. 28 is a view of the fluid channel of FIG. 23, with a barrier fluid disposed both upstream and downstream of each of a plurality of different droplet packets, to provide separation between different types of droplets, in accordance with aspects of the present disclosure.

FIGS. 26-28 illustrate use of barrier fluid 3568 to reduce the variation in cycle times among the droplets, to decrease or eliminate the incidence of straggler droplets, to reduce dispersion (spreading out) of a set of droplets along the fluid channel, to maintain separation of different sets of droplets, and/or to form a detectable boundary between different sets of droplets, among others.

FIG. 26 shows fluid channel 3570 containing a separator or barrier 3578 formed by a volume or partition, such as a slug 3580, of barrier fluid 3568 disposed downstream of a set or packet of droplets 3576. As fluid flows along channel 3570, slug 3580 may function as an impeding fluid that forms a moving barrier to the leading droplets, indicated at 3582. In other words, since the leading droplets cannot fuse with, or pass, the barrier, these leading droplets may tend to pile up behind the barrier, which limits dispersion of the droplets along the fluid channel.

FIG. 27 shows fluid channel 3570 with slug 3580 of barrier fluid 3568 disposed upstream of a set of droplets 3576. As fluid flows along channel 3570, slug 3580 may function as a pushing fluid or a scrubber that forms a moving barrier to the trailing droplets, indicated at 3584. In other words, these trailing droplets may tend to pile up ahead of the slug, which limits dispersion of the droplets along the fluid channel and prevents straggler droplets from mixing with other sets of droplets.

The separator or barrier formed by the barrier fluid may have any suitable size and shape. For example, the volume of the separator/barrier may be greater than that of each droplet (e.g., at least about 2, 5, or 10 times greater). The volume may, in some cases, be sufficient to form a separator with a diameter defined by the inner diameter of the fluid channel. Accordingly, the separator/barrier may be shaped according to the fluid channel, such as to produce a cylindrical separator and/or a separator that extends along the fluid channel by a distance that is at least about one or two droplet diameters, among others. The distance that the separator extends along the fluid channel may be defined in terms of the inner diameter of the fluid channel (e.g., at least about 1, 2, 5, or 10 times greater). A cylindrical separator may be a right cylinder, with substantially parallel leading (downstream) and/or trailing (upstream) interfaces with the carrier fluid, as shown in the drawings. Alternatively, the leading and/or trailing interfaces may be arcuate, for example, due to the gradient in fluid velocities across the channel. The volume may, in other cases, be insufficient for the separator/barrier to extend to the wall of the fluid channel, such that the inner diameter of the fluid channel is greater than the diameter of the separator/barrier, to form a relatively larger barrier droplet that defines a boundary for the position of relatively smaller sample droplets along the fluid channel. Accordingly, the separator/barrier may be spherical or substantially spherical (e.g., oblately spheroidal or ellipsoidal) in shape.

FIG. 28 shows fluid channel 3570 with separators 3578 (e.g., slugs 3580) disposed both upstream and downstream of distinct sets 3586, 3588 of droplets. In this case, the separators may provide separation between different types 3590, 3592 of droplets. The leading end and/or trailing end of a set of droplets may be identified with the aid of the separators. For example, each separator may be detectably distinguishable from droplets and/or the carrier fluid, such as by an optical or electrical characteristic of the separator (e.g., a distinct fluorescence, absorbance, polarization, electrical resistance, etc.). In some embodiments, the separator may contain a dye, such as a fluorescent dye.

Example 7

Selected System Embodiments

This example describes additional aspects of exemplary thermocycling systems in accordance with aspects of the present disclosure, presented without limitation as a series of numbered sentences.

1. A method of performing a flow-based reaction on a sample in droplets, comprising: (A) providing a plurality of segments defining at least two temperature regions; (B) operating a plurality of heating elements to maintain each temperature region at a different desired temperature; and (C) transporting droplets in a fluid channel extending along a helical path that passes through the temperature regions multiple times such that droplets traveling along the fluid channel are heated and cooled cyclically.

2. The method of paragraph 1, wherein the step of operating a plurality of heating elements includes a step of transferring heat to and/or from a temperature region with a thermoelectric cooler.

3. The method of paragraph 2, wherein the step of providing includes a step of providing a body member configured as a heat source and a heat sink, and wherein the step of operating a plurality of heating elements includes a step of transferring heat between the body member and a temperature region with the thermoelectric cooler.

4. The method of paragraph 3, wherein the body member is a core.

5. The method of paragraph 3 or paragraph 4, wherein the step of operating a plurality of heating elements includes a step of maintaining the body member at a temperature that is between a pair of the desired temperatures, and/or wherein the step of maintaining the body member includes a step of heating the body member with a resistive heater.

6. The method of claim 1, wherein the step of transporting droplets includes a step of transporting droplets in a high-density flow regime in which the droplets are packed closely together along and across the fluid channel such that the droplets travel along the fluid channel as a unit.

7. The method of any one of paragraphs 1 to 6, wherein the step of transporting droplets includes a step of transporting droplets along a continuous portion of the fluid channel that is maintained at a same desired temperature for one or more revolutions of the fluid channel about a central linear axis defined by the helical path.

8. The method of any one of paragraphs 1 to 7, wherein the step of transporting droplets results in amplifying a nucleic acid.

9. A method of performing a flow-based reaction on a sample in droplets, comprising: (A) providing a plurality of segments defining at least two temperature regions; (B) operating a plurality of heating elements to maintain each temperature region at a different desired temperature; and (C) transporting droplets in a fluid channel along a path that passes through the temperature regions multiple times such that the droplets are heated and cooled cyclically, wherein the step of transporting droplets is performed with the droplets disposed in a carrier fluid and positioned upstream, downstream, or both upstream and downstream of a barrier fluid that forms a moving barrier to droplet dispersion along the fluid channel.

10. The method of paragraph 9, wherein the step of transporting droplets is performed with the carrier fluid and the barrier fluid composed of respective oils that are immiscible with one another.

11. The method of paragraph 9, wherein the step of transporting droplets is performed with the barrier fluid being a gas.

12. The method of any one of paragraphs 9 to 11, wherein the fluid channel has an inner diameter, and wherein the moving barrier has a diameter defined by the inner diameter of the fluid channel.

13. The method of any one of paragraphs 9 to 12, wherein the transported droplets are relatively smaller droplets, and wherein the step of transporting is performed with the moving barrier being a relatively larger droplet.

14. The method of any one of paragraphs 9 to 13, wherein the step of transporting droplets includes a step of transporting a first set of droplets and a second set of droplets, and wherein the first set and the second set are separated from each other by the barrier fluid.

15. The method of paragraph 14, wherein each of the first set and the second set of droplets is bounded both upstream and downstream by the barrier fluid.

16. The method of paragraph 14 or paragraph 15, wherein the first set and the second set of droplets are configured to amplify different target molecules during the step of transporting droplets.

17. The method of any one of paragraphs 9 to 16, wherein the path is a helical path.

18. The method of any one of paragraphs 9 to 16, wherein the path is a planar path.

19. A thermocycling system for performing a flow-based reaction on a sample in droplets, comprising: (A) a droplet generator that produces droplets disposed in a carrier fluid; (B) a plurality of segments defining at least two temperature regions; (C) a plurality of heating elements configured to maintain each temperature region at a different desired temperature; and (D) a fluid channel including an inlet and an outlet and being connected or connectable to the droplet generator for introduction of droplets into the fluid channel, the fluid channel extending along a helical path that passes through each temperature region multiple times such that travel of the droplets along the fluid channel from the inlet to the outlet heats and cools the droplets cyclically.

20. The thermocycling system of paragraph 19, further comprising a reservoir holding a barrier fluid and configured to permit introduction of a volume of the barrier fluid into the fluid channel, to form a moving barrier to droplet dispersion along the fluid channel.

21. The thermocycling system of paragraph 19 or paragraph 20, wherein at least one of the heating elements is a thermoelectric cooler operatively disposed to transfer heat to and/or from a temperature region.

22. The thermocycling system of any one of paragraphs 19 to 21, further comprising a body member, wherein at least one independently controllable and distinct thermoelectric cooler is disposed between each segment and the body member.

23. The thermocycling system of paragraph 22, wherein the body member is a core, wherein the segments collectively define a central opening, and wherein the core is disposed in the central opening.

24. The thermocycling system of any one of paragraphs 19 to 23, wherein the fluid channel has a larger diameter closer to the inlet and a smaller diameter closer to the outlet.

25. The thermocycling system of any one of paragraphs 19 to 24, wherein the helical path extends about a central axis, and wherein at least one temperature region varies in size along the central axis.

26. A thermocycling system for performing a flow-based reaction on a sample in fluid, comprising: (A) a plurality of segments defining at least two temperature regions; (B) a plurality of heating elements configured to maintain each temperature region at a different desired temperature, at least one of the heating elements being a thermoelectric cooler operatively disposed to transfer heat to and/or from a temperature region; and (C) a fluid channel extending along a helical path that passes through each temperature region multiple times such that fluid flowing in the fluid channel is heated and cooled cyclically.

27. The thermocycling system of paragraph 26, further comprising one or more other discrete fluid channels extending along one or more helical paths that pass through the temperature regions multiple times such that fluid flowing in the one or more other fluid channels is heated and cooled cyclically.

28. The thermocycling system of paragraph 26 or paragraph 27, wherein the thermoelectric cooler is operatively disposed to transfer heat between a pair of the segments.

29. The thermocycling system of any one of paragraphs 26 to 28, further comprising a body member configured as a heat source, wherein the thermoelectric cooler is operatively disposed to transfer heat between the temperature region and the body member.

30. The thermocycling system of paragraph 29, wherein the body member is a core, wherein the segments collectively define a central opening, and wherein the core is disposed in the central opening.

31. The thermocycling system of any one of paragraphs 26 to 30, wherein the fluid channel changes in diameter one or more times as the fluid channel extends through the temperature regions multiple times.

32. The thermocycling system of paragraph 31, wherein the fluid channel includes an inlet and an outlet and has a larger diameter closer to the inlet and a smaller diameter closer to the outlet.

33. A thermocycling system for performing a flow-based reaction on a sample in fluid, comprising: (A) a body member configured as a heat source and a heat sink; (B) a plurality of segments defining at least two temperature regions; (C) a plurality of heating elements configured to maintain each temperature region at a different desired temperature, at least one of the heating elements being a thermoelectric cooler operatively disposed to transfer heat between the body member and at least one temperature region; and (D) a fluid channel extending along a helical path that passes through each temperature region multiple times such that fluid flowing in the channel is heated and cooled cyclically.

34. The thermocycling system of paragraph 33, wherein the body member is a core, wherein the segments collectively define a central opening, and wherein the core is disposed in the central opening.

35. The thermocycling system of paragraph 33 or paragraph 34, wherein the fluid channel includes fluidic tubing wrapped around the segments.

36. The thermocycling system of paragraph 35, wherein the fluidic tubing is disposed in grooves formed by the segments along the helical path.

37. The thermocycling system of paragraph 36, wherein the grooves include sloping edge contours.

38. The thermocycling system of paragraph 36 or paragraph 37, further comprising a cover disposed on the segments over the fluidic tubing, the cover defining an aperture that permits the fluidic tubing to extend into the grooves from outside the cover at any of a plurality of discrete groove positions along the aperture.

39. The thermocycling system of paragraph 38, wherein the segments are inner segments, and wherein the cover is formed by a plurality of outer segments.

40. The thermocycling system of any one of paragraphs 35 to 39, wherein the fluidic tubing includes a plurality of discrete tubes each extending along a same portion of the helical path.

41. The thermocycling system of any one of paragraphs 33 to 40, wherein the segments are inner segments, further comprising a plurality of outer segments attached to the inner segments with the fluid channel disposed between the inner segments and the outer segments.

42. The thermocycling system of any paragraph 33 or paragraph 34, wherein the segments include external grooves, and wherein the fluid channel is defined by the grooves and by a fluid tight sheet wrapped around the segments.

43. The thermocycling system of any one of paragraphs 33 to 42, wherein the thermoelectric cooler is positioned between the body member and the at least one temperature region.

44. The thermocycling system of any one of paragraphs 33 to 43, wherein at least one independently controllable and distinct thermoelectric cooler is disposed between each segment and the body member.

45. The thermocycling system of any one of paragraphs 33 to 44, wherein the body member includes a plurality of sections, each independently in thermal contact with a different one of the segments.

46. The thermocycling system of any one of paragraphs 33 to 45, wherein a resistive heater is operatively connected to at least one segment.

47. The thermocycling system of any one of paragraphs 33 to 46, wherein a distinct resistive heater is operatively connected to each segment.

48. The thermocycling system of any one of paragraphs 33 to 47, wherein a resistive heater is operatively connected to the body member.

49. The thermocycling system of any one of paragraph 33 to 48, wherein the helical path extends about a central axis, and wherein at least one temperature region varies in size along the central axis.

50. The thermocycling system of any one of paragraphs 33 to 49, wherein the fluid channel has a different path length for successive passes through at least one temperature region, thereby changing how much time a fluid portion spends in the at least one temperature region during the successive passes, if the fluid portion travels along the helical path at a uniform speed.

51. The thermocycling system of any one of paragraphs 33 to 50, wherein each of the segments is attached to the body member.

52. The thermocycling system of any one of paragraphs 33 to 51, further comprising a droplet generator operatively connected to the fluid channel for introduction of droplets into the fluid channel.

53. A method of performing a flow-based reaction on a sample in fluid, comprising: (A) providing a plurality of segments defining at least two temperature regions; (B) operating a plurality of heating elements to maintain each temperature region at a different desired temperature, at least in part by transferring heat to and/or from a temperature region with a thermoelectric cooler; and (C) transporting fluid in a fluid channel extending along a helical path that passes through each temperature region multiple times such that fluid flowing in the fluid channel is heated and cooled cyclically.

54. The method of paragraph 53, wherein the step of providing includes a step of providing a body member configured as a heat source and a heat sink, and wherein the step of operating includes a step of transferring heat between the body member and a temperature region with a thermoelectric cooler.

55. The method of paragraph 54, wherein the body member is a core.

56. The method of paragraph 54 or paragraph 55, wherein the step of operating a plurality of heating elements includes a step of maintaining the body member at a temperature that is between a pair of the desired temperatures.

57. The method of paragraph 56, wherein the step of maintaining the body member includes a step of heating the body member with a resistive heater.

58. The method of any one of paragraphs 53 to 57, wherein the step of transporting fluid includes a step of transporting fluid along a continuous portion of the fluid channel that is maintained at a same desired temperature for one or more revolutions of the fluid channel about a central axis of the helical path.

59. The method of any one of paragraphs 53 to 58, wherein the step of transporting fluid includes a step of transporting droplets disposed in fluid.

60. The method of any one of paragraphs 53 to 59, wherein the step of transporting fluid results in amplifying a nucleic acid.

61. A method of performing a flow-based reaction on a sample in fluid, comprising: (A) providing a plurality of segments defining at least two temperature regions; (B) operating a plurality of heating elements to maintain each temperature region at a different desired temperature; and (C) transporting fluid in a fluid channel extending along a helical path that passes through each temperature region multiple times such that fluid flowing in the fluid channel is heated and cooled cyclically for a plurality of cycles each having a duration, wherein the duration of each of two or more of the cycles at a beginning of the plurality of cycles is longer than the duration of each remaining cycle.

62. The method of paragraph 61, wherein the step of transporting fluid causes a portion of the fluid to traverse the temperature regions more slowly for the two or more cycles and then traverse the temperature regions more quickly for each remaining cycle.

63. The method of paragraph 61 or paragraph 62, wherein a portion of the fluid travels relatively farther for each of the two or more cycles and then travels relatively shorter for each remaining cycle.

64. The method of any one of paragraphs 61 to 63, wherein a portion of the fluid travels through a relatively wider region of the fluid channel for the two or more cycles and then travels through a relatively narrower region of the fluid channel for each remaining cycle.

65. The method of any one of paragraphs 61 to 64, wherein the fluid channel includes an inlet and an outlet, and wherein additional fluid is introduced into the fluid channel at a position between the inlet and the outlet after the fluid channel has extended through the two or more cycles and before extending through the remaining cycles.

66. The method of any one of paragraphs 61 to 65, wherein the step of transporting fluid includes a step of transporting droplets disposed in fluid.

67. The method of any one of paragraphs 61 to 66, wherein the step of transporting fluid results in amplifying target molecules.

68. The method of any one of paragraphs 61 to 67, wherein the step of operating a plurality of heating elements includes a step of operating a thermoelectric cooler.

69. The method of any one of paragraphs 61 to 68, wherein the remaining cycles outnumber the two or more cycles.

70. The method of any one of paragraphs 61 to 69, where at least eight remaining cycles are performed.

71. The method of any one of paragraphs 61 to 70, wherein the number of temperature regions varies along the central axis such that the fluid channel extends through two or more of the remaining cycles for each revolution of the fluid channel about a central axis of the helical path.

72. A thermocycling system for performing a flow-based reaction on a sample in fluid, comprising: (A) a plurality of segments defining at least two temperature regions; (B) a plurality of heating elements configured to maintain each temperature region at a different desired temperature; and (C) a fluid channel extending along a helical path that traverses each temperature region multiple times such that fluid flowing in the channel is heated and cooled cyclically, wherein the fluid channel has a different path length for at least a pair of successive passes through at least one temperature region, thereby changing how much time a fluid portion spends in the at least one temperature region during each of the successive passes, if the fluid portion travels along the fluid channel at a uniform speed.

73. The thermocycling system of paragraph 72, wherein the helical path extends about a central axis, and wherein at least one temperature region varies in size along the central axis.

74. The thermocycling system of paragraph 72 or paragraph 73, wherein the fluid channel includes an inlet and an outlet, and wherein a length of the helical path per revolution about a central axis of the helical path decreases substantially continuously between the inlet and the outlet.

75. The thermocycling system of paragraph 74, wherein the segments collectively form a frustoconical shape.

76. The thermocycling system of paragraph 72 or paragraph 73 wherein the fluid channel includes an inlet and an outlet, and wherein a length of the helical path per revolution about a central axis of the helical path decreases stepwise at least once between the inlet and the outlet.

77. The thermocycling system of paragraph 72 or paragraph 73, wherein the helical path corresponds to a cylindrical shape.

78. The thermocycling system of any one of paragraphs 72 to 77, wherein the plurality of segments includes a different number of segments at different positions along a central axis of the helical path.

79. The thermocycling system of any one of paragraphs 72 to 78, wherein the fluid channel includes an inlet and an outlet, wherein fluid flowing in the fluid channel from the inlet to the outlet at a constant volume rate of flow is heated and cooled cyclically for a plurality of cycles proceeding in order and each having a duration, and wherein the duration of each of two or more of the cycles at a beginning of the order is longer than the duration of each remaining cycle of the order.

80. A thermocycling system for performing a flow-based reaction on a sample in fluid, comprising: (A) a plurality of segments defining a plurality of temperature regions; (B) a plurality of heating elements configured to maintain each temperature region at a different desired temperature; and (C) a fluid channel extending along a helical path defining a central axis, the fluid channel passing through the temperature regions multiple times such that fluid flowing in the channel is heated and cooled cyclically, wherein the number of temperature regions varies along the central axis.

81. The thermocycling system of paragraph 80, wherein a continuous portion of the fluid channel is maintained at a same desired temperature for one or more revolutions of the fluid channel about the central axis.

82. The thermocycling system of paragraph 81, wherein the continuous portion is a first continuous portion, wherein a second continuous portion of the fluid channel passes through each of the temperature regions multiple times, and wherein a third continuous portion of the fluid channel is separated from the first portion by the second portion and is maintained at a same desired temperature for one or more revolutions of the fluid channel about the central axis.

83. The thermocycling system of any one of paragraphs 80 to 82, wherein the fluid channel includes an inlet and an outlet, wherein fluid flowing from the inlet to the outlet is heated and cooled cyclically over a plurality of cycles, and wherein the number of cycles per revolution of the fluid channel increases toward the outlet.

84. The thermocycling system of paragraph 83, wherein the fluid channel provides only one cycle per revolution closer to the inlet and two or more cycles per revolution closer to the outlet.

The systems disclosed herein may be combined, optionally, with apparatus, methods, compositions, and/or kits, or components thereof, described in the references listed above under Cross-References and incorporated herein by reference, particularly U.S. Pat. No. 7,041,481, issued May 9, 2006; U.S. Provisional Patent Application Ser. No. 61/194,043, filed Sep. 23, 2008; U.S. Provisional Patent Application Ser. No. 61/206,975, filed Feb. 5, 2009; U.S. Provisional Patent Application Ser. No. 61/277,200, filed Sep. 21, 2009; and U.S. patent application Ser. No. 12/586,626, filed Sep. 23, 2009.

The disclosure set forth above may encompass multiple distinct inventions with independent utility. Although each of these inventions has been disclosed in its preferred form(s), the specific embodiments thereof as disclosed and illustrated herein are not to be considered in a limiting sense, because numerous variations are possible. The subject matter of the inventions includes all novel and nonobvious combinations and subcombinations of the various elements, features, functions, and/or properties disclosed herein. The following claims particularly point out certain combinations and subcombinations regarded as novel and nonobvious. Inventions embodied in other combinations and subcombinations of features, functions, elements, and/or properties may be claimed in applications claiming priority from this or a related application. Such claims, whether directed to a different invention or to the same invention, and whether broader, narrower, equal, or different in scope to the original claims, also are regarded as included within the subject matter of the inventions of the present disclosure.

The invention claimed is:

1. A thermocycling system for performing a flow-based reaction on a sample in fluid, comprising:

a thermally conductive core configured as a heat source and a heat sink;

a plurality of segments surrounding and discrete from the core and defining at least two temperature regions;

a plurality of heating elements configured to maintain each temperature region at a different desired temperature, at least one of the heating elements being a thermoelectric cooler disposed between the core and one of the segments and configured to transfer heat between the core and the one segment; and a fluid channel extending along a helical path that passes through each temperature region multiple times such that fluid flowing in the channel is heated and cooled cyclically.

2. The thermocycling system of claim 1, wherein the segments collectively define a central opening, and wherein the core is disposed in the central opening.

3. The thermocycling system of claim 1, wherein the fluid channel includes fluidic tubing wrapped around the segments.

4. The thermocycling system of claim 3, wherein the fluidic tubing is disposed in grooves formed by the segments along the helical path.

5. The thermocycling system of claim 4, wherein the grooves include sloping edge contours.

6. The thermocycling system of claim 4, further comprising a cover disposed on the segments over the fluidic tubing, the cover defining an aperture that permits the fluidic tubing to extend into the grooves from outside the cover at any of a plurality of discrete groove positions along the aperture.

7. The thermocycling system of claim 6, wherein the segments are inner segments, and wherein the cover is formed by a plurality of outer segments.

8. The thermocycling system of claim 3, wherein the fluidic tubing includes a plurality of discrete tubes each extending along a same portion of the helical path.

9. The thermocycling system of claim 1, wherein the segments are inner segments, further comprising a plurality of outer segments attached to the inner segments with the fluid channel disposed between the inner segments and the outer segments.

10. The thermocycling system of claim 1, wherein the segments include external grooves, and wherein the fluid channel is defined by the grooves and by a fluid tight sheet wrapped around the segments.

11. The thermocycling system of claim 1, wherein at least one independently controllable and distinct thermoelectric cooler is disposed between each segment and the core.

12. The thermocycling system of claim 1, wherein the core includes a plurality of sections, each independently in thermal contact with a different one of the segments.

13. The thermocycling system of claim 1, wherein a resistive heater is operatively connected to at least one segment.

14. The thermocycling system of claim 13, wherein a distinct resistive heater is operatively connected to each segment.

15. The thermocycling system of claim 1, wherein a resistive heater is operatively connected to the core.

16. The thermocycling system of claim 1, wherein the helical path extends about a central axis, and wherein at least one temperature region varies in size along the central axis.

17. The thermocycling system of claim 1, wherein the fluid channel has a different path length for successive passes through at least one temperature region, thereby changing how much time a fluid portion spends in the at least one temperature region during the successive passes, if the fluid portion travels along the helical path at a uniform speed.

18. The thermocycling system of claim 1, wherein each of the segments is attached to the core.

19. The thermocycling system of claim 1, further comprising a droplet generator operatively connected to the fluid channel for introduction of droplets into the fluid channel.

20. The thermocycling system of claim 1, wherein the fluid channel changes in diameter one or more times as the fluid channel extends through the temperature regions multiple times.

21. The thermocycling system of claim 20, wherein the fluid channel includes an inlet and an outlet and has a larger diameter closer to the inlet and a smaller diameter closer to the outlet.

* * * * *